US008252546B2

(12) United States Patent
Briles et al.

(10) Patent No.: US 8,252,546 B2
(45) Date of Patent: Aug. 28, 2012

(54) DIAGNOSING PNEUMOCOCCAL PNEUMONIA

(75) Inventors: David E. Briles, Birmingham, AL (US); Susan K. Hollingshead, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 434 days.

(21) Appl. No.: 12/377,440

(22) PCT Filed: Aug. 17, 2007

(86) PCT No.: PCT/US2007/076172
§ 371 (c)(1), (2), (4) Date: Apr. 6, 2009

(87) PCT Pub. No.: WO2008/022299
PCT Pub. Date: Feb. 21, 2008

(65) Prior Publication Data
US 2010/0227341 A1 Sep. 9, 2010

Related U.S. Application Data

(60) Provisional application No. 60/822,715, filed on Aug. 17, 2006, provisional application No. 60/827,348, filed on Sep. 28, 2006, provisional application No. 60/917,178, filed on May 10, 2007.

(51) Int. Cl.
*G01N 33/569* (2006.01)
(52) U.S. Cl. ............. 435/7.34; 435/7.1; 435/7.2; 435/6; 435/7.92
(58) Field of Classification Search .................. None
See application file for complete search history.

(56) References Cited

U.S. PATENT DOCUMENTS

| | | | |
|---|---|---|---|
| 5,792,457 A | 8/1998 | Tuomanen et al. | |
| 6,027,734 A | 2/2000 | Briles et al. | |
| 6,217,884 B1 | 4/2001 | Sampson et al. | |
| 6,245,335 B1 | 6/2001 | Masure et al. | |
| 6,312,944 B1 | 11/2001 | Russell et al. | |
| 6,500,613 B1 | 12/2002 | Briles et al. | |
| 6,514,503 B1 | 2/2003 | Gizurarson et al. | |
| 6,565,856 B1 | 5/2003 | Skeiky et al. | |
| 6,573,082 B1 | 6/2003 | Choi et al. | |
| 6,592,876 B1 | 7/2003 | Briles et al. | |
| 6,635,246 B1 | 10/2003 | Barrett et al. | |
| 6,699,703 B1 | 3/2004 | Doucette-Stamm et al. | |
| 6,784,164 B2 | 8/2004 | Masure et al. | |
| 7,202,056 B2 | 4/2007 | Lee et al. | |
| 7,384,775 B2 | 6/2008 | Zagursky et al. | |
| 7,635,487 B2 | 12/2009 | Meinke et al. | |
| 2005/0020813 A1 | 1/2005 | Masignani et al. | |
| 2006/0264378 A1 | 11/2006 | Fujii et al. | |
| 2008/0085277 A1 | 4/2008 | Cho et al. | |
| 2011/0130300 A1 | 6/2011 | Ochs-Onolemhemhen et al. | |

FOREIGN PATENT DOCUMENTS

| | | |
|---|---|---|
| EP | 1630230 | 3/2006 |
| WO | WO00/06737 | 2/2000 |
| WO | WO00/76541 | 12/2000 |
| WO | WO02/077021 | 10/2002 |
| WO | WO02/083855 | 10/2002 |
| WO | WO2004/092209 | 10/2004 |

OTHER PUBLICATIONS

Hava et al (Mol.Microbiol. 2002. 45: 1389-1406.*
Gillespie et al (J.Clin.Pathol. 1995. 48: 803-806).*
Glover et al., "*Streptococcus pneumoniae* surface protein PcpA elicits protection against lung infection and fatal sepsis" *Infection and Immunity* 76(6):2767-2776 (2008).
Johnston et al., "Mn2+-dependent regulation of multiple genes in *Streptococcus pneumoniae* through PsaR and the resultant impact on virulence" *Infection and Immunity* 74(2):1171-1180 (2006).
Scott et al., "Diagnosis of pneumococcal pneumonia by PsaA PCR analysis of lung aspirates from adult patients in Kenya" *Journal of Clinical Microbiology* 41(6):2554-9 (2003).
Tharpe et al., "Purification and seroreactivity of pneumococcal surface adhesin A (PsaA)" *Clinical and Diagnostic Laboratory Immunology* 3(2):227-229 (1996).
Toikka et al., "Pneumolysin PCR-based diagnosis of invasive pneumococcal infection in children" *Journal of Clinical Microbiology* 37(3):633-7 (1999).
Zysk et al., "Immune response to capsular polysaccharide and surface proteins of *Streptococcus pneumoniae* in patients with invasive pneumococcal disease" *Journal of Infectious Diseases* 187(2):330-3 (2003).
Amsbaugh et al., "Genetic Control of the Antibody Response to Type III Pneumococcal Polysaccharide in Mice," J. Exp. Med. 136:931-949 (1972).
Avery et al., "Studies on the Chemical Nature of the Substance Inducing Transformation of Pneumococcal Types," J. Exp. Med. 149:297-326 (1979).
Balachandran et al., "Role of pneumococcal surface protein C in nasopharyngeal carriage and pneumonia and its ability to elicit protection against carriage of *Streptococcus pneumoniae*," Infect. Immun. 70:2526-34 (2002).
Belanger et al., "Pyruvate oxidase is a determinant of Avery's rough morphology," J. Bacteriol. 186:8164-71 (2004).
Berry et al., "Cloning and expression of the pneumococcal neuraminidase gene in *Escherichia coli*," Gene 71:299-305 (1988).
Berry et al., "Cloning and Characterization of nanB, a Second *Streptococcus pneumoniae* Neuraminidase Gene, and Purification of the NanB Enzyme from Recombinant *Escherichia coli*," J. Bacteriol. 178(16):4854-4860 (1996).

(Continued)

*Primary Examiner* — Jennifer Graser
(74) *Attorney, Agent, or Firm* — McKeon, Meunier, Carlin & Curfman, LLC

(57) ABSTRACT

Compositions and methods for eliciting an immune response against *Streptococcus pneumoniae* are described. More particularly, the present disclosure relates to immunogenic PcpA polypeptides, including fragments of PcpA and variants thereof, and nucleic acids that encode the polypeptides. The present disclosure further relates to methods of making and using the immunogenic polypeptides. Further provided is a method of diagnosing pneumococcal infection (e.g., pneumonia) in a subject by obtaining a biological sample from the subject and detecting one or more pneumococcal antigens that are selectively expressed during invasion (e.g., PcpA or fragments thereof).

10 Claims, 9 Drawing Sheets

OTHER PUBLICATIONS

Berry et al., "Additive Attenuation of Virulence of *Streptococcus pneumoniae* by Mutation of the Genes Encoding Pneumolysin and Other Putative Pneumococcal Virulence Proteins," Infect. Immun. 68:133-140 (2000).

Black et al., "Efficacy, safety and immunogenicity of heptavalent pneumococcal conjugate vaccine in children. Northern California Kaiser Permanente Vaccine Study Center Group," Pediatr. Infect. Dis. J. 19:187-195 (2000).

Black et al., "Effectiveness of heptavalent pneumococcal conjugate vaccine in children younger than five years of age for prevention of pneumonia," Pediatr. Infect. Dis. 21:810-5 (2002).

Black et al., "Clinical effectiveness of seven-valent pneumococcal conjugate vaccine (Prevenar) against invasive pneumococcal diseases: prospects for children in France," Arch. Pediatr. 11:843-53 (2004).

Bogaert et al., "*Streptococcus pneumoniae* colonization: the key to pneumococcal disease," Lancet Infect. Dis. 4:144-54 (2004).

Briles et al., "Mouse Igg3 antibodies are highly protective against infection with *Streptococcus pneumoniae*," Nature 294(5836):88-90 (1981).

Briles et al., "Antiphosphocholone Antibodies Found in Normal Mouse Serum are Protective Against Intravenous Infection with Type 3 *Streptococcus pneumoniae*," J. Exp. Med. 153:694-705 (1981).

Briles et al., "The effects of idiotype on the ability of IgG1 antiphosphorylcholine antibodies to protect mice from fatal infection with *Streptococcus pneumoniae*," Eur. J. Immunol. 14:1027-1030 (1984).

Briles et al., "The effects of subclass on the ability of antiphosphocholine antibodies to protect mice from fatal infection with *Streptococcus pneumoniae*," J. Mol. Cell. Immunol. 1:305-309 (1984).

Briles et al., "Genetic control of the susceptibility to pneumococcal infection," Curr. Top. Microbiol. Immunol. 124:103-120 (1986).

Briles et al., "Antipneumococcal Effects of C-Reactive Protein and Monoclonal Antibodies to Penumococcal Cell Wall and Capsular Antigens," Infect. Immun. 57(5):1457-1464 (1989).

Briles et al., "Strong association between capsular type and virulence for mice among human isolates of *Streptococcus pneumoniae*," Infect. Immun. 60:111-6 (1992).

Briles et al., "Immunizations with pneumococcal surface protein A and pneumolysin are protective against pneumonia in a murine model of pulmonary infection with *Streptococcus pneumoniae*," J. Infect. Dis. 188::339-48 (2003).

Briles et al, "Nasal colonization with *Streptococcus pneumoniae* includes subpopulation of surface and invasive pneumococci," Infect. Immun. 73:6945-51 (2005).

Brooks-Walter et al., "The pspC gene of *Streptococcus pneumoniae* encodes a polymorphic protein, PspC, which elicits cross-reactive antibodies to PspA and provides immunity to pneumococcal bacteremia," Infect. Immun. 67:6533-6542 (1999).

Camara et al., "A neuraminidase from *Streptococcus pneumoniae* has the features of a surface protein," Infect. Immun. 62:3688-3695 (1994).

Coats et al., "Antibodies to the pneumococcal surface protein A, PspA, can be produced in splenectomized and can protect splenectomized mice from infection with *Streptococcus pneumoniae*," Vaccine 23:4257-62 (2005).

Crennell et al., "Crystal structure of a bacterial sialidase (from *Salmonella typhimurium* LT2) shows the same fold as an influenza virus neuraminidase," Proc. Natl. Acad. Sci. USA 90(21):9852-9856 (1993).

Di Fabio et al., "Evolution of *Streptococcu pneumoniae* serotypes and penicillin susceptibility in Latin America. Sireva-Vigia Group. 1993 to 1999. PAHO Sireva-Vigia Study Group. Pan American Health Organization," Pediatr. Infect. Dis. J. 20:959-67 (2001).

Enright and Spratt, "A multilocus sequence typing scheme for *Streptococcus pneumoniae*: identification of clones associated with serious invasive disease," Microbiology 144:3049-60 (1998).

Eskola et al., "Efficacy of Pneumococcal Conjugate Vaccine against acute otitis media," N. Engl. J. Med. 344:403-409 (2001).

Fedson and Scott, "The burden of pneumococcal disease among adults in developed and developing countries: what is and is not known," Vaccine 17:S11-18 (Suppl. 1) (1999).

Fedson and Musher, "Pneumococcal Polysaccharide Vaccine," in Vaccines, Plotkin and Orenstein (eds) 529-88 (2004).

Gillespie et al., "Detection of C-polysaccharide in serum of patients with *Streptococcus pneumoniae* bacteraemia," J. Clin. Pathol. 48:803-6 (1995).

Hakenbeck et al, "Antigenic variation of penicillin-binding proteins from penicillin-resistant clinical strains of *Streptococcus pneumoniae*," J. Infect. Dis. 164:313-9 (1991).

Hakenbeck et al., "Variability of penicillin-binding proteins from penicillin-sensitive *Streptococcus pneumoniae*," J. Infect. Dis. 164:307-12 (1991).

Hava and Camilli, "Large-scale identification of serotype 4 *Streptococcus pneumoniae* virulence factors," Mol. Microbiol. 45:1389-1406 (2002).

Hava et al., "From nose to lung: the regulation behind *Streptococcus pneumoniae* virulence factors," Mol. Micro. 50:1103-10 (2003).

Hoskins et al., "Genome of the bacterium *Streptococcus pneumoniae* strain R6," J. Bact. 183:5709-5717 (2001).

Jedrzejas, "Pneumococcal virulence factors: structure and function," Microbiol. Mol. Biol. Rev. 65(2):187-207 (2001).

Johnston et al., "$Mn^{2+}$-dependent regulation of multiple genes in *Streptococcus pneumoniae* through PsaR and the resultant impact on virulence," Infect. Immun. 74:1171-80 (2006).

Kelly et al., "Neuraminidase activities of clinical isolates of *Diplococcus pneumoniae*," J. Bacteriol. 94:272-273 (1967).

King et al., "Phase variable desialylation of host proteins that bind to *Streptococcus pneumoniae* in vivo and protect the airway," Mol. Micro. 54:159-171 (2004).

LaMarco et al., "Experimental alteration of chinchilla middle ear mucosae by bacterial neuraminidase," Ann. Otol. Rhinol. Laryngol. 95:304-308 (1986).

Lau et al., "A functional genomic analysis of type 3 *Streptococcus pneumoniae* virulence," Mol. Micro. 40:555-71 (2001).

Lock et al., "Purification and immunological characterization of neuraminidase produced by *Streptococcus pneumoniae*," Microb. Pathog. 4:33-43 (1988).

Lock et al., "Comparative efficacy of pneumococcal neuraminidase and pneumolysin as immunogens protective against *Streptococcus pneumoniae*," Microb. Pathog. 5:461-467 (1988).

Long et al., "Immunization with native or recombinant *Streptococcus pneumoniae* neuraminidase affords protection in the chinchilla otitis media model," Infect. Immun. 72:4309-4313 (2004).

Madhi and Klugman, "A role for *Streptococcus pneumoniae* in virus-associated pneumonia," Nat. Med. 10:811-813 (2004).

Magee and Yother, "Requirement for capsule in colonization by *Streptococcus pneumoniae*" Infect. Immun. 69:3755-3761 (2001).

Manco et al., "Pneumococcal neuraminidases A&B both have essential roles during infection of the respiratory trackt & sepsis," Infect. Immun. 74(7):4014-4020 (2006).

Martinot et al., "Haemolytic-Uraemic syndrome associated with *Streptococcus pneumoniae* meningitis," Euro. J. Pediatr. 148(7):648-649 (1989).

Mbelle et al., "Immunogenicity and impact on masopharyngeal carriage of a nonavalent pneumococcal conjugate vaccine," J. Infect. Dis. 180:1171-6 (1999).

McCullers and Bartmess, "Role of neuraminidase in lethal synergism between influenza virus and *Streptococcus pneumoniae*," J. Infect. Dis. 187:1000-1009 (2003).

McDaniel et al., "A protective monoclonal antibody that reacts with a novel antigen of pneumococcal teichoic acid," Microb. Pathog. 3:249-260 (1987).

Mulholland, "The Gambian pneumococcal vaccine trial-implications for control of childhood pneumonia," Trop. Med. Int. Health 10:497-500 (2005).

Ogunniyi et al., "Immunization of mice with combinations of pneumococcal virulence proteins elicits enhanced protection against challenge with *Streptococcus pneumoniae*," Infect. Immun. 68:3028-33 (2000).

Orihuela et al., "Tissue-specific contributions of pneumococcal virulence factors to pathogenesis," J. Infect. Dis. 190:1661-9 (2004).

Ostergaard and Andersen, "Etiology of community-acquired pneumonia. Evaluation by transtracheal aspiration, blood culture, or serology," Chest 104:1400-7 (1993).

O'Toole et al., "Neuraminidase activity in bacterial meningitis," J. Clin. Invest. 50:979-985 (1971).

Ottolenghi and Hotchkiss, "Appearance of genetic transforming activity in pneumococcal cultures," Science 132:1257-8 (1960).

Paton et al., "Molecular analysis of the pathogenicity of *Streptococcus pneumoniae*: the role of pneumococcal proteins," Annu. Rev. Microbiol. 47:89-115 (1993).

Paton et al., "Molecular analysis of putative pneumococcal virulence proteins," Microb. Drug Resist. 3:1-10 (1997).

Quagliarello et al., "Bacterial meningitis: pathogenesis, pathophysiology, and progress," N. Eng. J. Med. 327:864-72 (1992).

Ren et al., "Both family 1 and family 2 PspA proteins can inhibit complement deposition and confer virulence to a capsular serotype 3 strain of *Streptococcus pneumoniae*," Infect. Immun. 71:75-85 (2003).

Ren et al., "Effects of PspA and antibodies to PspA on activation and deposition of complement on the pneumococcal surface," Infect. Immun. 72:114-22 (2004).

Roach et al., "The evolution of vertebrate Toll-like receptors," Proc. Natl. Acad. Sci. USA 102:9577-82 (2005).

Robinson et al., "Clones of *Streptococcus pneumoniae* isolated from nasopharyngeal carriage and invasive disease in young children in central Tennessee," J. Infect. Dis. 183:1501-7 (2001).

Roche et al., "Relative roles of genetic background and variation in PspA in the ability of antibodies to PspA to protect against capsular type 3 and 4 strains of *Streptococcus pneumoniae*," Infect. Immun. 71:4498-505 (2003).

Sanchez-Beato et al., "Molecular characterization of PCPA: a novel choline-binding protein of *Streptococcus pneumoniae*," FEMS Micro. Letters 164:207-14 (1998).

Scanlon et al., "Purification and properties of *Streptococcus pneumoniae* neuraminidase," Enzyme 41(3):143-150 (1989).

Shakhnovich et al., "Neuraminidase expressed by *Streptococcus pneumoniae* desialylates the lipopolysaccharide of *Neisseria meningitidis* and *Haemophilus influenzae*: a paradigm for interbacterial competition among pathogens of the human respiratory tract," Infect. Immun. 70:7161-7164 (2002).

Shapiro et al., "The protective efficacy of polyvalent pneumococcal polysaccharide vaccine," N. Eng. J. Med. 325:1453-60 (1991).

Sharper et al., "PspA protects *Streptococcus pneumoniae* from killing by Apolactoferrin and antibody to PspA enhances killing of Pneumococci by Apolactoferrin," Infect. Immun. 72:5031-40 (2004).

Takashima et al., "Role of tumor necrosis factor alpha in pathogenesis of pneumococcal pneumonia in mice," Infect. Immun. 65:257-60 (1997).

Tettelin et al., "Nasal lymphoid tissue (NALT) as a mucosal immune inductive site," Science 293:498-506 (2001).

Tong et al., "Comparison of structural changes of cell surface carbohydrates in the eustachian tube epithelium of chinchillas infected with a *Streptococcus pneumoniae* neuraminidase-deficient mutant or its isogenic parent strain," Microb. Pathog. 31:309-317 (2001).

Tong et al., "Evaluation of the virulence of a *Streptococcus pneumoniae* neuraminidase-deficient mutant in nasopharyngeal colonization and development of otitis media in the chinchilla model," Infect. Immun. 68:921-924 (2000).

Van Ginkel et al., "Cutting edge: the mucosal adjuvant cholera toxin redirects vaccine proteins into olfactory tissues," J. Immunol. 165:4778-4782 (2000).

Van Ginkel et al., "Pneumococcal carriage results in ganglioside-mediated olfactory tissue infection," Proc. Natl. Acad. Sci. USA 100:14363-14367 (2003).

Wu et al., "Nasal lymphoid tissue (NALT) as a mucosal immune inductive site," Scand. J. Immunol. 46:506-513 (1997).

Wu et al., "Intranasal immunization of mice with PspA (pneumococcal surgace protein A) can prevent intranasal carriage, pulmonary infection, and sepsis with *Streptococcus pneumoniae*," J. Infect. Dis. 175:839-48 (2003).

Pother et al., "Protection of mice from infection with *Streptococcus pneumoniae* by anti-phosphocholine antibody," Infect. Immun. 36:184-188 (1982).

Yother et al., "Transformation of encapsulated *Streptococcus pneumoniae*," J. Bacteriol. 168:1463-1465 (1986).

Yother et al., "Truncated forms of PspA that are secreted from *Streptococcus pneumoniae* and their use in functional studies and cloning of the pspA gene," J. Bacteriol. 174:610-618 (1992).

Yother and White, "Novel surface attachment mechanism of the *Streptococcus pneumoniae* protein PspA," J. Bacteriol. 176:2976-85 (1994).

Denapaite et al., "The genome of Streptococcus mitis B6—what is a commensal?," PLoS One 5(2):e9426 (2010).

Gor et al., "Relationship between surface accessibility for PpmA, PsaA, and PspA and antibody-mediated immunity to systemic infection by *Streptococcus pneumoniae*," Infect. Immun. 73:1304-12 (2005).

Hakenbeck et al., "Versatility of choline metabolism and choline-binding proteins in *Streptococcus pneumoniae* and commensal streptococci," FEMS Microbiol. Rev. 33:572-86 (2009).

Ogunniyi et al., "Central role of manganese in regulation of stress responses, physiology and metabolism in *Streptococcus pneumoniae*," J. Bacteriology (published online Jul. 2, 2010).

Wu, et al., "Establishment of a *Streptococcus pneumoniae* nasopharyngeal colonization model in adult mice" Microb. Pathog. 23:127-137 (1997).

Yesilkaya et al., "Identification of amino acids essential for catalytic activity of pneumococcal neuraminidase A" Research in Microbiology 157:569-574 (2006).

\* cited by examiner

DIAGNOSING PNEUMOCOCCAL PNEUMONIA

CROSS-REFERENCE TO RELATED APPLICATIONS

The present application claims priority to U.S. Ser. No. 60/822,715, filed Aug. 17, 2006; U.S. Ser. No. 60/827,348, filed Sep. 28, 2006; and U.S. Ser. No. 60/917,178, filed May 10, 2007, which are incorporated by reference herein in their entireties.

STATEMENT REGARDING FEDERALLY SPONSORED RESEARCH

This invention was made with government support under Grant No. R01 AI021548 from the National Institutes of Health. The government has certain rights in the invention.

BACKGROUND

*Streptococcus pneumoniae* is a rather ubiquitous human pathogen, which can infect several organs including lungs, the central nervous system (CNS), the middle ear, and the nasal tract. Infection results in various symptoms such as bronchitis, pneumonia, meningitis, sinus infection, and sepsis. *S. pneumoniae* is a major cause of bacterial meningitis in humans and is associated with significant mortality and morbidity despite antibiotic treatment (Quagliarello et al., (1992) N. Eng. J. Med. 327: 864-872).

There are two currently available pneumococcal vaccines. One is a vaccine for adults composed of 23 different capsular polysaccharides, which together represent the capsular types of about 90% of strains causing pneumococcal infection. This vaccine, however, is not immunogenic in children, an age group with high susceptibility to pneumococcal infection. In adults the vaccine has been shown to be about 60% efficacious against bacteremic pneumonia, but it is less efficacious in adults at higher risk of pneumococcal infection because of age or underlying medical conditions (Fedson, and Musher. 2004. "Pneumococcal Polysaccharide Vaccine," pp. 529-588. In *Vaccines*. S. A. Plotkin and W. A. Orenstein (eds.), W. B. Saunders and Co., Philadelphia, Pa.; Shapiro et al., *N. Engl. J. Med.* 325:1453-1460 (1991)). This vaccine has not been shown to be effective against non-bacteremic pneumococcal pneumonia, the most common form of infection.

The second available vaccine is a 7-valent conjugate vaccine that is efficacious against bacteremic pneumococcal infections in children less than 2 years of age. It has also demonstrated efficacy against pneumonia (Black et al., *Pediatr Infect. Dis.* 21:810-5 (2002); Black et al., *Arch. Pediatr.* 11 (7):843-53 (2004)). The production of this vaccine is complicated because of the need to produce 7 different conjugates, which leads to the vaccine being expensive (about $200/child). Moreover, the vaccine does not do a good job of covering infections in the developing world where non-vaccine types of *Streptococcus pneumoniae* are very common (Di Fabio et al., *Pediatr. Infect. Dis. J.* 20:959-967 (2001); Mulholland, *Trop. Med. Int. Health* 10:497-500 (2005)). This vaccine does not work as well against otitis media and colonization as it does against invasive disease. It has also been shown that the use of the 7-valent conjugate vaccine has led to an increase in colonization and disease with strains of capsule types not represented by the 7 polysaccharides included in the vaccine (Bogaert et al., *Lancet Infect. Dis.* 4:144-154 (2004); Eskola et al., *N. Engl. J. Med.* 344:403-409 (2001); Mbelle et al., *J. Infect. Dis.* 180:1171-1176 (1999)). Therefore, a need remains for effective treatments for *Streptococcus pneumoniae*. There are also limited diagnostic assays available for *Streptococcus pneumonoiae*.

The standard procedure for diagnosing pneumonia is based on clinical presentation, pulmonary consolidation seen by X-ray and a positive blood culture for *Streptococcus pneumoniae*. Unfortunately this method misses between 75 and 85 percent of patients with pneumococcal pneumonia because many subject have no pneumococci in their blood. An antigen detection assay that detects a cell wall polysaccharide is more sensitive but unfortunately leads to many false positives because pneumococci can be present in the nasal passages of subjects without being present in their lungs or blood.

SUMMARY

Compositions and methods for diagnosing *Streptococcus pneumoniae* are described. More particularly, the present disclosure relates to antigenic PcpA polypeptides, including fragments of PcpA and variants thereof, and nucleic acids that encode the polypeptides. The present disclosure further relates to methods of making and using the antigenic polypeptides of any pneumococcal antigen that is produced during invasive disease but not during nasal colonization. Further provided is a method of diagnosing pneumococcal infection (e.g., pneumonia) in a subject by obtaining a biological sample from the subject and detecting one or more pneumococcal antigens that are selectively expressed during invasion (e.g., PcpA or fragments thereof). These compositions and methods offer improved efficacy and efficiency and reduced cost as compared to presently available compositions and methods designed to diagnose pneumococcal infection.

DETAILED DESCRIPTION

Figure 1:
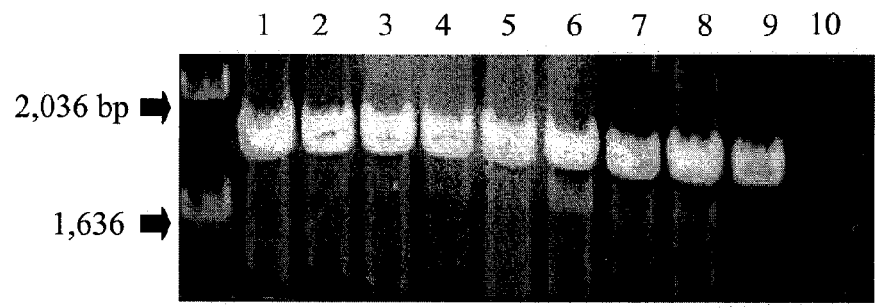
FIG. 1 shows PCR confirmation of pcpA. PCR analysis of genomic DNA of various *S. pneumoniae* strains. Primer pair (BGP1 (SEQ ID NO:45) and BGP2 (SEQ ID NO:46)) were used to amplify the nucleic acid encoding the N-terminal portion of PcpA (including the LRR region). Lane 1, TIGR4; Lane 2, L82013; Lane 3, D1091B; Lane 4, BG12730; Lane 5, TJ0893; Lane 6, R6; Lane 7, BG10752; Lane 8, V175; Lane 9, EF3030; Lane 10, negative control (no template DNA).

Immunogenic fragments and variants of PcpA are described herein along with methods of making and using the fragments and variants. PcpA, which was initially identified as a choline binding protein (CBP) of *Streptococcus pneumoniae*, differs from the CBP proteins PspA and PspC (Sanchez-Beato et al., *FEMS Microbiol. Lett.* 164:207-214 (1998)), and mutations in pcpA have been shown to cause (1) reduced virulence in the lung, in bacteremia, and in the nasopharynx of mice in competition models in which a mutant strain and a wild type strain are allowed to compete (Hava and Camilli, *Mol. Microbiol.* 45:1389-1406 (2002)); (2) reduced virulence and bacterial load in a non-competition comparison of lung sepsis (Johnston et al., *Infect. Immun.* 74:1171-1180 (2006)); (3) reduced ability of the invasive strain TIGR4 (capsular type 4) *S. pneumoniae* to cause sepsis in CBA/CaHN-Btkxid/J mice; and (4) reduced lung colonization in competition with wild type strains. The present disclosure provides the first evidence that PcpA is immunogenic and, in particular, that fragments and variants of PcpA are immunogenic. The present disclosure also provides the first evidence that PcpA is import for invasion of *S. pneumoniae* into the lung (i.e., lung infection) but not for colonization of *S. pneumoniae* in nasal passages.

Immunogenic polypeptides comprise the full-length PcpA amino acid sequence (in the presence or absence of the signal sequence), fragments thereof, and variants thereof. Full-length PcpA includes GenBank Accession No. CAB04758 from *Streptococcus pneumoniae* strain B6, GenBank Accession No. NP_346554 from *S. pneumoniae* strain TIGR4 and GenBank Accession No. NP_359536 from *S. pneumoniae* strain R6.

Optionally, immunogenic polypeptides of PcpA comprise one or more leucine rich regions (LRRs). These LRRs are present in naturally occurring PcpA or have about 60 to about 99% sequence identity, including, for example, 80%, 85%, 90% or 95% sequence identity to the naturally occurring LRRs. LRRs in the mature PcpA protein (i.e., the protein lacking the signal peptide) can be found within SEQ ID NOs:1, 2, or 41.

An immunogenic polypeptide of PcpA optionally lacks the choline binding anchor sequence typically present in the naturally occurring mature PcpA protein. The naturally occurring sequence of the choline binding anchor is SEQ ID NO:47 of the mature PcpA protein. More particularly, an immunogenic polypeptide comprises an N-terminal region of naturally occurring PcpA with one or more amino acid substitutions and about 60 to about 99% sequence identity or any identity in between, e.g., 80, 85, 90 and 95% identity, to the naturally occurring PcpA. The N-terminal region may comprise the amino acid sequence of SEQ ID NOs:1, 2, 3, 4, or 41, in the presence or absence of one or more conservative amino acid substitutions and in the presence or absence of the signal sequence. The N-terminal region may comprise an amino acid sequence having about 60 to about 99% sequence identity (or any identity in between 80 to 99% identity) to SEQ ID NOs:1, 2, 3, 4, or 41.

Immunogenic fragments of SEQ ID NOs:1, 2, 3, 4, or 41 comprise 5, 10, 20, 30, 40, 50, 60, 70, 80, 90, 100, 110, 120, 130, 140, 150, 160, 170, 180, 190 and 191 amino acid residues of SEQ ID NOs:1, 2, 3, 4, or 41 or any number of amino acid residues between 5 and 191. Examples of such fragments include, by way of example, amino acids comprising LEKIE-DRAFD (SEQ ID NO:5), FSELEEIELP (SEQ ID NO:6), ASLEYIGTSA (SEQ ID NO:7), FSFSQKLKKL (SEQ ID NO:8), TFSSSSKLEL (SEQ ID NO:9), ISHEAFANLS (SEQ ID NO:10), NLEKLTLPKS (SEQ ID NO:11), VKTLGSN-LFR (SEQ ID NO:12), LTTSLNMLML (SEQ ID NO:13), LTTSLKHVDV (SEQ ID NO:14), RGMIVASVDG (SEQ ID NO:15), EEGNESFASVDG (SEQ ID NO:16), VSFQSK-TQLI (SEQ ID NO:17), VLFSKDKTQLI (SEQ ID NO:18), YYPSQKNDES (SEQ ID NO:19), YKTPKETKEL (SEQ ID NO:20), ASYSFNKNSY (SEQ ID NO:21), LKKLELNEGL (SEQ ID NO:22), QKIGTFAFAD (SEQ ID NO:23), EKIGT-FAFAD (SEQ ID NO:24), ATKLEEISLP (SEQ ID NO:25), AIKLEEISLP (SEQ ID NO:26), NSLETIERLA (SEQ ID NO:27), FYGNLELKELIL (SEQ ID NO:28).

Optionally, immunogenic polypeptides of PcpA lack the LRRs. Examples of immunogenic polypeptides lacking the LRR include SEQ ID NO:29, SEQ ID NO:30, and SEQ ID NO:31 or any immunogenic fragment of either SEQ ID NOs: 29, 30 or 31 comprising 5 or more amino acid residues. SEQ ID NOs:30 and 31 comprise the residues C-terminal to the leucine-rich region of PcpA.

Variants of the immunogenic polypeptides described herein may comprise one or more conservative amino acid substitutions. Variants of the immunogenic polypeptides include amino acid sequence having about 60 to about 99% sequence identity (or any identity in between 60 and 99% identity) to SEQ ID NOs:1 to 31, and 41 or any fragment thereof. Variants are selected for their immunogenic capacity using methods taught herein.

The immunogenic polypeptides of PcpA described herein include fragments of PcpA and variants of such fragments. Variants of PcpA fragments may comprise amino acid sequence modifications. For example, amino acid sequence modifications include substitutional, insertional or deletional changes. Substitutions, deletions, insertions or any combination thereof may be combined in a single variant so long as the variant is an immunogenic polypeptide. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known and include, but are not limited to, M13 primer mutagenesis and PCR mutagenesis. Amino acid substitutions are typically of single residues but can occur at a number of different locations at once. Substitutional variants are those in which at least one residue has been removed and a different residue inserted in its place. Such substitutions generally are made in accordance with the following Table 1 and are referred to as conservative substitutions. However, others are well known to those of skill in the art.

TABLE 1

Conservative Amino Acid Substitutions

| Original Residue | Exemplary Substitutions |
| --- | --- |
| Arg | Lys |
| Asn | Gln |
| Asp | Glu |
| Cys | Ser |
| Gln | Asn |
| Glu | Asp |
| Gly | Pro |
| His | Gln |
| Ile | Leu, Val |
| Leu | Ile, Val |
| Lys | Arg, Gln |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Variants as used herein may also include naturally occurring pcpA alleles from alternate strains that exhibit polymorphisms at one or more sites within the homologous pcpA gene. Variants can be produced by conventional molecular biology techniques. The variants are described herein relative to sequence identity as compared to the naturally occurring pcpA. Those of skill in the art readily understand how to determine the sequence identity of two polypeptides or nucleic acids. For example, the sequence identity can be calculated after aligning the two sequences so that the identity is at its highest level. Alignments are dependent to some extent upon the use of the specific algorithm in alignment programs. This could include, for example, the local homology algorithm of Smith and Waterman *Adv. Appl. Math.* 2: 482 (1981), the homology alignment algorithm of Needleman and Wunsch, *J. Mol Biol.* 48: 443 (1970), by the search for similarity method of Pearson and Lipman, *PNAS USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), BLAST and BLAST 2.0 and algorithms described by Altschul et al., *Nucleic Acids Res.* 25:3389-3402, 1977; Altschul, et al., *J. Mol. Biol.* 215:403-410, 1990; Zuker, M. *Science* 244:48-52, 1989; Jaeger et al. *PNAS USA* 86:7706-7710, 1989 and Jaeger et al. *Methods Enzymol.* 183:281-306, 1989. Each of these references is incorporated by reference at least for the material related to alignment and calculation of identity. It is understood that any of the methods typically can be used and that in certain instances the results of these various methods may differ. Where sequence identity is provided as, for example, 95%, then such identity must be detectable with at least one of the accepted methods of calculation.

The immunogenic polypeptides described herein can include one or more amino acid analogs or non-naturally occurring stereoisomers. These amino acid analogs and stereoisomers can readily be incorporated into polypeptide chains by charging tRNA molecules with the amino acid of choice and engineering genetic constructs that utilize, for example, amber codons, to insert the analog amino acid into a peptide chain in a site specific way (Thorson et al., *Methods in Molec. Biol.* 77:43-73 (1991), Zoller, *Current Opinion in Biotechnology*, 3:348-354 (1992); Ibba, *Biotechnology & Genetic Engineering Reviews* 13:197-216 (1995), Cahill et al., *TIBS*, 14 (10):400-403 (1989); Benner, *TIB Tech*, 12:158-163 (1994); Ibba and Hennecke, *Bio/technology*, 12:678-682 (1994) all of which are herein incorporated by reference at least for material related to amino acid analogs). Immunogenic fragments can be produced that resemble peptides but which are not connected via a natural peptide linkage. For example, linkages for amino acids or amino acid analogs can include CH2NH—, —CH2S—, —CH2-CH2-, —CH═CH—(cis and trans), —COCH2-, —CH(OH)CH2-, and —CHH2SO— (These and others can be found in Spatola, A. F. "Peptide backbone modifications: A structure-activity analysis of peptides containing amide bond surrogates, conformational constraints, and related backbone modifications." In *Chemistry and Biochemistry of Amino Acids, Peptides, and Proteins*, pp. 267-357. Weinstein, B. editor, Marcel Dekker, New York, N.Y. (1983); Morley, *Trends in Pharm. Sci.* 1 (2):463-468 (1980); Hudson, et al., *Int J Pept Prot Res* 14:177-185 (1979) (—CH2NH—, CH2CH2-); Spatola et al. *Life Sci* 38:1243-1249 (1986) (—CHH2-S); Hann, *Journal of the Chemical Society: Perkin Transactions* 1 pp. 307-314 (1982) (—CH—CH—, cis and trans); Almquist et al., *J. Med. Chem.* 23:1392-1398 (1980) (—COCH2-); Jennings-White et al., *Tetrahedron Lett* 23:2533 (1982) (—COCH2-); European Publication No. EP0045665 to Szelke, et al. (1982) (—CH(OH)CH2-); Holladay et al., *Tetrahedron. Lett* 24:4401-4404 (1983) (—C(OH)CH2-); and Hruby *Life Sci* 31:189-199 (1982) (—CH2-S—); each of which is incorporated herein by reference at least for the material regarding linkages).

Amino acid analogs and stereoisomers often have enhanced or desirable properties, such as, more economical production, greater chemical stability, enhanced pharmacological properties (half-life, absorption, potency, efficacy, etc.), altered specificity (e.g., a broad-spectrum of biological activities), and others. For example, D-amino acids can be used to generate more stable peptides, because D amino acids are not recognized by naturally occurring peptidases. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch *Ann. Rev. Biochem.* 61:387 (1992), incorporated herein by reference).

A composition comprising an immunogenic polypeptide of PcpA and a pharmaceutically acceptable carrier are described herein. Optionally, the composition further comprises an adjuvant. Compositions comprising the immunogenic polypeptide may contain combinations of other immunogenic polypeptides, including, for example, an immunogenic *Staphylococcus* polypeptide or immunogenic fragments of PspA, NanA, PsaA, pneumolysin, PspC, PotD or any combination thereof.

Optionally, the compositions described herein are suitable for administration to a mucosal surface. The composition can be a nasal spray, a nebulizer solution, or an aerosol inhalant, for example. Thus the composition may be present in a container and the container may be a nasal sprayer, a nebulizer, or an inhaler.

By pharmaceutically acceptable carrier is meant a material that is not biologically or otherwise undesirable, i.e., the material may be administered to a subject, along with the immunogenic fragment of PcpA, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in *Remington: The Science and Practice of Pharmacy*, 21$^{st}$ Edition, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally from about 5 to about 8 or from about 7 to about 7.5. Other carriers include sustained release preparations such as semipermeable matrices of solid hydrophobic polymers containing the immunogenic PcpA polypeptides. Matrices are in the form of shaped articles, e.g., films, liposomes or microparticles. It will be apparent to those persons skilled in the art that certain carriers may be more preferable depending upon, for instance, the route of administration and concentration of composition being administered. Carriers are those suitable for administration of the PcpA immunogenic fragments to humans or other subjects.

Pharmaceutical compositions may include carriers, thickeners, diluents, buffers, preservatives, surface active agents, adjuvants, immunostimulants, in addition to the immunogenic polypeptide. Pharmaceutical compositions may also include one or more active ingredients such as antimicrobial agents, anti-inflammatory agents and anesthetics.

Adjuvants include metallic salts, such as aluminium salts, and are well known in the art as providing a safe excipient with adjuvant activity. The mechanism of action of these adjuvants are thought to include the formation of an antigen depot such that antigen may stay at the site of injection for up to 3 weeks after administration, and also the formation of antigen/metallic salt complexes which are more easily taken up by antigen presenting cells. In addition to aluminium, other metallic salts have been used to adsorb antigens, including salts of zinc, calcium, cerium, chromium, iron, and beirilium. The hydroxide and phosphate salts of aluminium are the most common. Formulations or compositions containing aluminium salts, antigen, and an additional immunostimulant are known in the art. An example of an immunostimulant is 3-de-O-acylated monophosphoryl lipid A (3D-MPL).

The adjuvant and/or immunostimulant can be administered concomitantly with the polypeptide composition, immediately prior to, or after administration of the composition. Optionally, the composition further comprises the adjuvant. Adjuvant formulations include, for example, an agent that targets mucosal inductive sites. The adjuvant may optionally be selected from the group including, but not limited to, cytokines, chemokines, growth factors, angiogenic factors, apoptosis inhibitors, and combinations thereof. When a cytokine is chosen as an adjuvant, the cytokine may be selected from the group including, but not limited to, interleukins including IL-1, IL-3, IL-2, IL-5, IL-6, IL-12, IL-15 and IL-18; transforming growth factor-beta (TGF-β); granulocyte macrophage colony stimulating factor (GM-CSF); interferon-gamma (IFN-γ); or any other cytokine that has adjuvant activity. Portions of cytokines, or mutants or mimics of cytokines (or combinations thereof), having adjuvant activity or other biological activity can also be used in the compositions and methods of the present invention.

When a chemokine is chosen as an adjuvant, the chemokine may optionally be selected from a group including, but not limited to, Lymphotactin, RANTES, LARC, PARC, MDC, TAR C, SLC and FKN. When an apoptosis inhibitor is chosen as an adjuvant, the apoptosis inhibitor may optionally be selected from the group including, but not limited to, inhibitors of caspase-8, and combinations thereof. When an angiogenic factor is chosen as an adjuvant, the angiogenic factor may optionally be selected from the group including, but not limited to, a basic fibroblast growth factor (FGF), a vascular endothelial growth factor (VEGF), a hyaluronan (HA) fragment, and combinations thereof.

Other examples of substantially non-toxic, biologically active adjuvants include hormones, enzymes, growth factors, or biologically active portions thereof. Such hormones, enzymes, growth factors, or biologically active portions thereof can be of human, bovine, porcine, ovine, canine, feline, equine, or avian origin, for example, and can be tumor necrosis factor (TNF), prolactin, epidermal growth factor (EGF), granulocyte colony stimulating factor (GCSF), insulin-like growth factor (IGF-1), somatotropin (growth hormone) or insulin, or any other hormone or growth factor whose receptor is expressed on cells of the immune system.

Adjuvants also include bacterial toxins, e.g., the cholera toxin (CT), the *E. coli* heat-labile toxin (LT), the *Clostridium difficile* toxin A and the pertussis toxin (PT), or combinations, subunits, toxoids, chimera, or mutants thereof. For example, a purified preparation of native cholera toxin subunit B (CTB) can be used. Fragments, homologs, derivatives, and fusions to any of these toxins are also suitable, provided that they retain adjuvant activity. Suitable mutants or variants of adjuvants are described, e.g., in WO 95/17211 (Arg-7-Lys CT mutant), WO 96/6627 (Arg-192-Gly LT mutant), and WO 95/34323 (Arg-9-Lys and Glu-129-Gly PT mutant). Additional LT mutants that can be used in the methods and compositions include, e.g., Ser-63-Lys, Ala-69-Gly, Glu-110-Asp, and Glu-112-Asp mutants. Other adjuvants, such as RH3-ligand; CpG-motif oligonucleotide; a bacterial monophosphoryl lipid A (MPLA) of, e.g., *E. coli, Salmonella minnesota, Salmonella typhimurium*, or *Shigella exseri*; saponins (e.g., QS21), or polylactide glycolide (PLGA) microspheres, can also be used. Possible other adjuvants are defensins and CpG motifs.

Provided are methods of making and using the immunogenic polypeptides described herein and compositions useful in such methods. The polypeptides can be generated using standard molecular biology techniques and expression systems. (See, for example, *Molecular Cloning: A Laboratory Manual, Third Edition* by Sambrook et al., Cold Spring Harbor Press, 2001). For example, a fragment of the pcpA gene that encodes an immunogenic polypeptide may be isolated and the polynucleotide encoding the immunogenic polypeptide may be cloned into any commercially available expression vector (such as pBR322 and pUC vectors (New England Biolabs, Inc., Ipswich, Mass.)) or expression/purification vectors (such as GST fusion vectors (Pfizer, Inc., Piscataway, N.J.)) and then expressed in a suitable prokaryotic, viral or eukaryotic host. Purification may then be achieved by conventional means or, in the case of a commercial expression/purification system, in accordance with a manufacturer's instructions.

Provided herein are nucleic acids comprising a sequence that encodes any one of SEQ ID NOs:1 to 31, and 41. Provided herein is a nucleic acid comprising SEQ ID NOs:32 and 33, which encode full length PcpA proteins or fragments thereof. Also provided are degenerate variants and fragments of these degenerate variants of SEQ ID NOs:32 and 33.

Nucleic acids that encode SEQ ID NOs:1 and 2 or fragments thereof are described, including SEQ ID NO:34 and SEQ ID NO:35, respectively, or degenerate variants or fragments thereof.

Nucleic acids that encode SEQ ID NOs:3 and 4 or fragments thereof include, but are not limited to, SEQ ID NOs:36 and 37, respectively, or degenerate variants or fragments thereof.

Nucleic acids that encode SEQ ID NO:41 or fragments thereof are described, including SEQ ID NO:42 or degenerate variants or fragments thereof.

Exemplary nucleic acids that encode SEQ ID NO:29 or fragments thereof include SEQ ID NO:38 or degenerate variants or fragments thereof.

More specifically, provided herein is a nucleic acid comprising any one of the sequences designated as SEQ ID NOs: 32 to 38, and 42 or degenerate variants thereof.

Also provided are isolated nucleic acids comprising a sequence that hybridizes under highly stringent conditions to all or any portion of a hybridization probe having a nucleotide sequence that comprises SEQ ID NOs:32 to 38, and 42 or the complement of SEQ ID NOs:32 to 38, and 42 or any fragment of the sequence or complement thereof. The hybridizing portion of the hybridizing nucleic acid is typically at least 15 (e.g., 15, 20, 25, 30, 40, or more) nucleotides in length. The hybridizing portion is at least 80% (e.g., 85%, 90% or 95%) identical to the a portion of the sequence to which it hybridizes. Hybridizing nucleic acids are useful, for example, as cloning probes, primers (e.g., PCR primer), or a diagnostic probe. Nucleic acid duplex or hybrid stability is expressed as the melting temperature or Tm, which is the temperature at which a probe dissociates from a target DNA. This melting temperature is used to define the required stringency conditions. If sequences are identified that are related and substantially identical to the probe, rather than identical, then it is useful to first establish the lowest temperature at which only homologous hybridization occurs with a particular concentration of salt (e.g., SSC or SSPE). Assuming that a 1% mismatching results in a 1° C. decrease in Tm, the temperature of the final wash in the hybridization reaction is reduced accordingly (for example, if sequences having more than 95% identity are sought, the final wash temperature is decreased by 5° C.). In practice, the change in Tm can be between 0.5 and 1.5° C. per 1% mismatch. Highly stringent conditions involve hybridizing at 68° C. in 5×SSC/5×Denhardt's solution/1.0% SDS, and washing in 0.2×SSC/0.1%

SDS at room temperature. Moderately stringent conditions include washing in 3×SSC at 42° C. Salt concentrations and temperatures can be varied to achieve the optimal level of identity between the probe and the target nucleic acid. Additional guidance regarding such conditions is readily available in the art, for example, in *Molecular Cloning: A Laboratory Manual, Third Edition* by Sambrook et al., Cold Spring Harbor Press, 2001.

Thus, it is understood that the nucleic acids that can encode the aforementioned peptide sequences, variants and fragments thereof are disclosed. This would include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

Also disclosed are vectors comprising the nucleic acids described herein. Thus, provided is a vector that comprises a nucleic acid that encodes an immunogenic polypeptide (e.g., SEQ ID NOs:1 to 31, or 41 or fragments or variants thereof). The vector can comprise any of the nucleic acid sequences SEQ ID NOs:32 to 38, and 42 or degenerate variants or fragments thereof. Optionally, the nucleic acid of the vector is operably linked to an expression control sequence (e.g., a promoter or enhancer or both). Suitable expression vectors are well known to those of skill in the art and commercially available from a variety of sources such as Novagen, Inc., Madison, Wis.; Invitrogen Corporation, Carlsbad, Calif.; and Promega Corporation, Madison, Wis.

A cultured cell comprising the vector is also provided. The cultured cell can be a cultured cell transfected with the vector or a progeny of the cell, wherein the cell expresses the immunogenic polypeptide. Suitable cell lines are known to those of skill in the art and are commercially available, for example, through the American Type Culture Collection (ATCC).

The transfected cells can be used in a method of producing an immunogenic polypeptide. The method comprises culturing a cell comprising the vector under conditions that allow expression of the immunogenic polypeptide, optionally under the control of an expression sequence. The immunogenic polypeptide can be isolated from the cell or the culture medium using standard protein purification methods.

The immunogenic polypeptides can be made using standard enzymatic cleavage of larger polypeptides or proteins or can be generated by linking two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). By peptide condensation reactions, native chemical ligation, solid phase chemistry, or enzymatic ligation, two fragments can be covalently joined via a peptide bond at their carboxyl and amino termini to form an immunogenic PcpA polypeptide. (*Synthetic Peptides: A User Guide.*, Grant, ed., W.H. Freeman and Co., New York, N.Y. (1992); *Principles of Peptide Synthesis.*, Bodansky and Trost, eds. Springer-Verlag Inc., New York, N.Y. (1993); Abrahmsen L et al., *Biochemistry*, 30:4151 (1991); Dawson et al. *Science,* 266:776-779 (1994); *Solid Phase Peptide Synthesis*, 2$^{nd}$ Edition, Stewart, ed., Pierce Chemical Company, Rockford, Ill., (1984), all of which are incorporated herein by reference for the methods described therein).

The immunogenic polypeptides and compositions comprising one or more polypeptides may be used to generate antibodies. Thus, a method of generating antibodies specific to PcpA in a subject comprises administering to the subject a immunogenic PcpA fragment described herein. Also provided herein are antibodies that bind the PcpA polypeptides as well as antibody fragments that bind the PcpA polypeptides.

Antibodies may be polyclonal or monoclonal, may be fully human or humanized, and include naturally occurring antibodies and single-chain antibodies. Antibodies can be made in vivo by administering to a subject an immunogenic PcpA polypeptide. Antibody production includes making monoclonal antibodies using hybridoma methods. Hybridoma methods are well known in the art and are described by Kohler and Milstein, *Nature,* 256:495 (1975) and Harlow and Lane. *Antibodies, A Laboratory Manual.* Cold Spring Harbor Publications, New York, (1988), which are incorporated by reference in their entirety for the methods described therein.

Methods for the production of single-chain antibodies are well known to those of skill in the art. See, for example, U.S. Pat. No. 5,359,046, (incorporated herein by reference in its entirety for such methods). A single chain antibody is created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation. See, for example, Huston, J. S., et al., *Methods in Enzym.* 203:46-121 (1991), which is incorporated herein by reference for its material regarding linkers.

Fully human and humanized antibodies to the PcpA polypeptides may be used in the methods described herein. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Transgenic animals (e.g., mice) that are capable, upon immunization, of producing a full repertoire of human antibodies (i.e., fully human antibodies) may be employed. The homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice results in the production of human antibodies upon antigen challenge (see, e.g., Jakobovits et al., *PNAS USA,* 90:2551-255 (1993); Jakobovits et al., *Nature,* 362:255-258 (1993); Bruggemann et al., *Year in Immuno.,* 7:33 (1993)). Human antibodies can also be produced in phage display libraries (Hoogenboom et al., *Jr. Mol. Biol.,* 227:381 (1991); Marks et al., *J. Mol. Biol.,* 222:581 (1991)). The techniques of Cote et al. and Boerner et al. also describe methods for the preparation of human monoclonal antibodies (Cole, et al., "The EBV-hybridoma technique and its application to human lung cancer." In, *Monoclonal Antibodies and Cancer Therapy,* Volume 27, Reisfeld and Sell, eds., pp. 77-96, Alan R. Liss, Inc., New York, N.Y., (1985); Boerner et al., *J. Immunol.*, 147 (1):86-95 (1991)). These references are incorporated by reference in their entirety for the methods described therein.

Antibody fragment as used herein includes F(ab')2, Fab', and Fab fragments, including hybrid fragments. Such fragments of the antibodies retain the ability to bind a specific PcpA polypeptide. Methods can be used to construct (ab) expression libraries (see e.g., Huse, et al., 1989 *Science* 246: 1275-1281) to allow rapid and effective identification of monoclonal F(ab) fragments with the desired specificity for a PcpA polypeptide. Antibody fragments that contain the idiotypes to the polypeptide may be produced by techniques known in the art including, but not limited to: (i) an F(ab')2 fragment produced by pepsin digestion of an antibody molecule; (ii) an Fab fragment generated by reducing the disulfide bridges of an F(ab')2 fragment; (iii) an F(ab) fragment generated by the treatment of the antibody molecule with papain and a reducing agent and (iv) F(v) fragments.

Described herein is a method of reducing the risk of a pneumococcal infection in a subject comprising administering to the subject the immunogenic fragment of PcpA or a composition thereof. Pneumococcal infections include, for example, meningitis, otitis media, pneumonia, sepsis, or hemolytic uremia. Thus, the risk of any one or more of these infections are reduced by the methods described herein. The method can further comprise the step of administering a second immunogenic fragment. The second immunogenic fragment can be from PspA, NanA, PsaA, pneumolysin, PspC, or any combination thereof. The second immunogenic fragment can be administered at the same time, before or after the immunogenic fragment of PcpA.

The compositions comprising a PcpA polypeptide or fragments thereof may be administered orally, parenterally (e.g., intravenously), intramuscularly, intraperitoneally, transdermally or topically, including intranasal administration or administration to any part of the respiratory system. As used herein, administration to the respiratory system means delivery of the compositions into the nose and nasal passages through one or both of the nares or through the mouth, including delivery by a spraying mechanism or droplet mechanism, through aerosolization or intubation.

The exact amount of the compositions and PcpA polypeptides or fragments required will vary from subject to subject, depending on the species, age, weight and general condition of the subject, the polypeptide used, and its mode of administration. Thus, it is not possible to specify an exact amount for every composition. However, an appropriate amount can be determined by one of ordinary skill in the art given the description herein. Furthermore, multiple doses of the PcpA polypeptide or fragment may be used including, for example, in a prime and boost regimen.

Combinations of PspA and pneumolysin are more efficacious that either protein alone at eliciting protective immunity against pneumonia and sepsis (Briles et al., *J. Infect. Immun.* 188:339-48 (2003); Ogunniyi et al., *Infect. Immun.* 68:3028-33 (2000)). Thus, the compositions comprising PcpA or immunogenic fragments can optionally comprise a second immunogenic fragment of PcpA, PspA, NanA, PsaA, pneumolysin, PspC, PhtE, PhtB or any combination thereof. These references are incorporated herein by reference in their entireties for methods of combining and methods of administration for the proteins taught therein.

Any of the aforementioned treatments can be used in any combination with the compositions described herein. Combinations may be administered either concomitantly (e.g., as an admixture), separately but simultaneously (e.g., via separate intravenous lines into the same subject), or sequentially (e.g., one of the compounds or agents is given first followed by the second). Thus, the term combination is used to refer to either concomitant, simultaneous, or sequential administration of two or more agents.

Also provided are methods of diagnosing pneumococcal pneumonia in a subject. Bacteremia is the "gold standard" for diagnosis of pneumococcal pneumonia, however less than 1 in 4 patients with pneumococcal pneumonia are thought to be bacteremic and are therefore not informative in vaccine trials or diagnosis. If a higher percentage of pneumococcal pneumonia patients could be accurately diagnosed, the size of the trials, treatment and thus their costs would be proportionately reduced. Antigen detection assays based on the detection of C-polysaccharide are plagued with two competing problems. One is that they are not sensitive enough to detect most of the patients with non-bacteremic pneumonia. The other problem is that they are sensitive enough to detect some individuals who are colonized but not infected with *S. pneumoniae*. Thus, making these assays more sensitive is not likely to greatly improve diagnosis of the non-bacteremic patients. The use of C-polysaccharide as a target antigen is especially problematic because it is made in higher levels by colonizing *S. pneumoniae* than invading *S. pneumoniae*.

To determine efficacy of pneumococcal vaccines to accurately diagnose, and to monitor treatment, it is necessary to know which subjects have pneumococcal pneumonia and which ones do not. The standard procedure for diagnosing pneumonia is by X-ray or other diagnostic tests and a positive blood culture for *Streptococcus pneumoniae*. Subjects satisfying these criteria are assumed to have pneumococcal pneumonia. Unfortunately this method misses between 75 and 85 percent of patients with pneumococcal pneumonia, because it has been estimated that only 15-25% of patients with pneumonia also have bacteremia (Fedson, et al., *Vaccine* 17: Suppl. 1:S11-18 (1999); Ostergaard and Andersen, *Chest* 104:1400-1407 (1993)).

One approach to solve this problem has been to use antigen detection assays that detect a cell wall polysaccharide in the urine. This assay is much more sensitive but unfortunately has false positives in 12% of adults and up to 60% of children. This is because the assay target is sometimes present in the urine because of nasal colonization with pneumococci in patients without pneumococcal disease in their lungs or blood.

Methods of detecting PcpA expression to diagnose pneumococcal pneumonia are provided. The major reservoir of pneumococci in the world resides in human nasal carriage. Acquisition of infection is generally from a carrier and infection is always preceded by nasal carriage. The colonization of the nasopharynx is considered a prerequisite for the spread of pneumococci to the lower respiratory tract, the nasal sinuses, and the middle ear. Expression of PcpA by *Streptococcus pneumoniae* is repressed by the regulator PsaR in response to high manganese (Mn2+) in the nasopharynx (Johnston, et al., *Infect. Immun.* 74:1171-1180 (2006)). Thus PcpA is only made and present on the surface of the pneumococcus when the organism has transitioned from its position in the nasopharynx into the lung where the manganese concentration is low. This is also true for other pneumococcal antigens including, but not limited to, surface antigen A (PsaA), PsaB, PsaC, rrgA (a gram positive anchor family protein), rrgB (a gram positive anchor family protein), rrgC, srtB, pyruvate formate acetyltransferase (pfl), septation ring formation regulator EzrA, SecA subunit (a preprotein translocase), StpK (a serine/threonine protein kinase), galactose-1-phosphate uridylytransferase (galT), ORF00431 sortase B, ORF00767, prtA (also known as ppmA and is a serine protease, subtilysin family protein) and psrP (a cell wall surface anchor family protein). The nucleic and amino acid sequences for these proteins are known and can be found at www.genbank.org and www.tigr.org.

Thus, provided are methods to detect a pneumococcal antigen that is only produced in the lung and blood but not in the nasal cavity. PcpA is only produced in areas of low Mn2+ concentration ($\leq 0.1$ µM) such as the lung and blood (Johnston, et al., *Infect. Immun.* 74:1171-1180 (2006)). Therefore PcpA is only made by pneumococci in the lung and blood but not by pneumococci on mucosal surfaces. Thus, colonization of pneumococci on mucosal surfaces would not be detected by the methods described herein and would therefore not lead to a false positive. By detecting pneumococcal antigens only produced in areas of low Mn2+ concentrations, only subjects with pneumonia would be diagnosed. Thus the present disclosure provides an advantageous method for diagnosing a subject with pneumonia or other pneumococcal infections like meningitis.

Thus provided are methods of diagnosing pneumococcal pneumonia in a subject comprising obtaining a biological sample from a subject and detecting in the biological sample the presence of one or more pneumococcal antigens selectively expressed during invasive disease, wherein the presence of the antigen indicates pneumococcal pneumonia in the subject. Also provided are methods of pneumococcal pneumonia in a subject comprising obtaining a biological sample from a subject and detecting in the biological sample the presence of one or more pneumococcal antigens expressed in the presence of high concentrations of Mn2+, wherein the presence of the antigen indicates pneumococcal pneumonia in the subject. The subject may or may not be bacteremic. Preferably, the antigen is not expressed or is not expressed in high quantities during colonization.

As used herein a biological sample which is subjected to testing is a sample derived from a subject such as a human and includes, but is not limited to, any biological fluid, preferably a bodily fluid. Examples of bodily fluids include, but are not limited to, whole blood, serum, urine, saliva, tissue infiltrate, pleural effusions, lung lavage fluid, bronchoalveolar lavage fluid, and the like. The biological fluid may be a cell culture medium or supernatant of cultured cells. For example, the sample can be a blood sample or a serum sample. Optionally, the biological sample is not from the nasal cavity of the subject.

The provided methods can also comprise the step of detecting in the biological sample the presence of C-polysaccharide. A ratio of PcpA to C-polysaccharide in the biological sample can also be determined.

Optionally, the ratio in bodily fluid of an antigen such as PcpA that is expressed only during invasive disease with an antigen such as neuraminidase A (NanA) that is expressed only during colonization is determined. This can be important since in virtually all colonization there may be a little bit of invasion and in virtually all pneumococcal pneumonia there is invariable also colonization. The ratio of the concentration of an invasive antigen such as PcpA to the concentration of a colonization antigen such as NanA will be low in subjects with colonization. For subjects with pneumococcal pneumonia this ratio should be high. By way of example only without meaning to be limiting, a ratio of 2:1, PcpA:NanA would indicate pneumococcal pneumonia in the subject while a ratio of 1:2, PcpA:NanA would indicate the subject does not have pneumococcal pneumonia. Examples of other antigens that may be markers of invasion include SmrC and PhoU, which have been found by others to be required for both pneumonia and sepsis but to play only a minimal role in colonization. An example of an antigen expressed primarily during colonization includes, but it not limited to, NanA, which is critical for colonization but plays little role in invasive disease. (Lau et al Mol. Micro. 40:555-571 (2001), Hava et al Mol Micro 50:1103-1110 (2003), Hava et al Mol. Micro. 45:1389-1406 (2002), Orihuela, et al J. Infect. Dis. 190:1661-1669 (2004)).

As used herein pneumococcal antigens selectively expressed during invasive disease refers to an antigen that is expressed in areas of low Mn2+ concentration. Such antigens have little to no expression during colonization of pneumococci on mucosal surfaces. The phrase pneumococcal antigens selectively expressed during invasive disease also refers to levels of a pneumococcal antigen, such as PcpA, that are at least 1.5 times higher in a biological sample from a subject being tested than in a control sample. As used throughout, higher, increases, enhances or elevates as compared to a control refer to increases above a control. For example, a control level can be the level of expression or activity in a control sample in the absence of a stimulus. A control sample as used herein includes a sample from a subject without pneumococcal pneumonia. Antigens that are selectively expressed in invasive disease or expressed in the presence of low concentrations of Mn2+ include, but are not limited to, PcpA, PsaA, PsaB, PsaC, rrgA, rrgB, rrgC, srtB, pfl, septation ring formation regulator EzrA, SecA subunit, StpK, galT, ORF00431, ORF00767, prtA and psrP. Optionally, one of the pneumococcal antigens detected in the provided methods is PcpA.

Assay techniques that can be used to determine levels of expression in a sample are well-known to those of skill in the art. Such assay methods include radioimmunoassays, reverse transcriptase PCR (RT-PCR) assays, immunohistochemistry assays, in situ hybridization assays, competitive-binding assays, Western Blot analyses, ELISA assays and proteomic approaches, two-dimensional gel electrophoresis (2D electrophoresis) and non-gel based approaches such as mass spectrometry or protein interaction profiling. Assays also include, but are not limited to, competitive and non-competitive assay systems using techniques such as radioimmunoassays, enzyme immunoassays (EIA), enzyme linked immunosorbent assay (ELISA), sandwich immunoassays, precipitin reactions, gel diffusion reactions, immunodiffusion assays, agglutination assays, complement-fixation assays, immunoradiometric assays, fluorescent immunoassays, protein A immunoassays, and immunoelectrophoresis assays. For examples of immunoassay methods, see U.S. Pat. No. 4,845,026 and U.S. Pat. No. 5,006,459.

For diagnostic methods, an antigen binding partner, for example, an antibody, can be labeled with a detectable moiety and used to detect the antigen in a sample. The antibody can be directly labeled or indirectly labeled (e.g., by a secondary or tertiary antibody that is labeled with a detectable moiety). Numerous labels are available including, but not limited to radioisotopes, fluorescent labels, and enzyme-substrate labels. Radioisotopes include, for example, $^{35}S$, $^{14}C$, $^{125}I$, $^{3}H$, and $^{131}I$. Fluorescent labels include, for example, rare earth chelates (europium chelates), fluorescein and its derivatives, rhodamine and its derivatives, dansyl, Lissamine, phycoerythrin and Texas Red. The labels can be conjugated to the antigen binding partner using the techniques disclosed in Current Protocols in Immunology, Volumes 1 and 2, Coligen et al., Ed., Wiley-Interscience, New York, N.Y., Pubs., (1991), for example.

When using enzyme-substrate labels, the enzyme preferably catalyses a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes are described in O'Sullivan et al., Methods for the Preparation of Enzyme-Antibody Conjugates for use in Enzyme Immunoassay, in Methods in Enzym. (ed J. Langone & H. Van Vunakis), Academic press, New York, 73: 147-166 (1981). Examples of enzyme-substrate combinations include, for example, horseradish peroxidase (HRPO) with hydrogen peroxidase as a substrate, alkaline phosphatase (AP) with para-Nitrophenyl phosphate as chromogenic substrate, and β-D-galactosidase (β-D-Gal) with a chromogenic substrate (e.g. p-nitrophenyl-β-D-galactosidase) or fluorogenic substrate 4-methylumbelliferyl-β-D-galactosidase.

In an ELISA assay, an antibody is prepared, if not readily available from a commercial source, specific to an antigen. In addition, a reporter antibody generally is prepared which binds specifically to the antigen. The reporter antibody is attached to a detectable reagent such as a radioactive, fluorescent or enzymatic reagent, for example horseradish peroxidase enzyme or alkaline phosphatase. To carry out the ELISA, antibody specific to antigen is incubated on a solid support, e.g., a polystyrene dish, that binds the antibody. Any free protein binding sites on the dish are then covered by incubating with a non-specific protein such as bovine serum albumin. Next, the sample to be analyzed is incubated in the dish, during which time the antigen binds to the specific antibody attached to the polystyrene dish. Unbound sample is washed out with buffer. A reporter antibody specifically directed to the antigen and linked to a detectable reagent such as horseradish peroxidase is placed in the dish resulting in binding of the reporter antibody to any antibody bound to the antigen. Unattached reporter antibody is then washed out. Reagents for peroxidase activity, including a colorimetric substrate are then added to the dish. Immobilized peroxidase, linked to antibodies, produces a colored reaction product. The amount of color developed in a given time period is proportional to the amount of antigen present in the sample. Quantitative results typically are obtained by reference to a standard curve.

A competition assay can also be employed wherein antibodies specific to antigen are attached to a solid support and labeled antigen and a sample derived from the subject or control are passed over the solid support. The amount of label detected which is attached to the solid support can be correlated to a quantity of antigen in the sample.

Of the proteomic approaches, 2D electrophoresis is a technique well known to those in the art. Isolation of individual proteins from a sample such as serum is accomplished using sequential separation of proteins by different characteristics usually on polyacrylamide gels. First, proteins are separated by size using an electric current. The current acts uniformly on all proteins, so smaller proteins move farther on the gel than larger proteins. The second dimension applies a current perpendicular to the first and separates proteins not on the basis of size but on the specific electric charge carried by each protein. Since no two proteins with different sequences are identical on the basis of both size and charge, the result of a 2D separation is a square gel in which each protein occupies a unique spot. Analysis of the spots with chemical or antibody probes, or subsequent protein microsequencing can reveal the relative abundance of a given protein and the identity of the proteins in the sample.

Optionally, a genetic sample from the biological sample can be obtained. The genetic sample comprises a nucleic acid, preferably RNA and/or DNA. For example, in determining the expression of genes mRNA can be obtained from the biological sample, and the mRNA may be reverse transcribed into cDNA for further analysis. Alternatively, the mRNA itself is used in determining the expression of genes.

A genetic sample may be obtained from the biological sample using any techniques known in the art (Ausubel et al. Current Protocols in Molecular Biology (John Wiley & Sons, Inc., New York, 1999); Molecular Cloning: A Laboratory Manual, 2nd Ed., ed. by Sambrook, Fritsch, and Maniatis (Cold Spring Harbor Laboratory Press: 1989); Nucleic Acid Hybridization (B. D. Hames & S. J. Higgins eds. 1984)). The nucleic acid may be purified from whole cells using DNA or RNA purification techniques. The genetic sample may also be amplified using PCR or in vivo techniques requiring subcloning. The genetic sample can be obtained by isolating mRNA from the cells of the biological sample and reverse transcribing the RNA into DNA in order to create cDNA (Khan et al. Biochem. Biophys. Acta 1423:17 28, 1999).

Once a genetic sample has been obtained, it can be analyzed for the presence or absence of one or more particular genes encoding pneumococcal antigens such as, for example, PcpA. Thus, pneumococcal antigens that can be assayed include, but are not limited to, PcpA, PsaA, PsaB, PsaC, rrgA, rrgB, rrgC, srtB, pfl, septation ring formation regulator EzrA, SecA subunit, StpK, galT, ORF00431, ORF00767, prtA and psrP or any combination thereof. The analysis may be performed using any techniques known in the art including, but not limited to, sequencing, PCR, RT-PCR, quantitative PCR, restriction fragment length polymorphism, hybridization techniques, Northern blot, microarray technology, DNA microarray technology, and the like. In determining the expression level of a gene or genes in a genetic sample, the level of expression may be normalized by comparison to the expression of another gene such as a well known, well characterized gene or a housekeeping gene. For example, reverse-transcriptase PCR (RT-PCR) can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA.

Hybridization to clones or oligonucleotides arrayed on a solid support (i.e., gridding) can be used to both detect the expression of and quantitate the level of expression of that gene. In this approach, a cDNA encoding an antigen is fixed to a substrate. The substrate may be of any suitable type including but not limited to glass, nitrocellulose, nylon or plastic. At least a portion of the DNA encoding the antigen is attached to the substrate and then incubated with the analyte, which may be RNA or a complementary DNA (cDNA) copy of the RNA, isolated from the sample of interest. Hybridization between the substrate bound DNA and the analyte can be detected and quantitated by several means including but not limited to radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

It must be noted that, as used in the specification and the appended claims, the singular forms a, an and the include plural referents unless the context clearly dictates otherwise. Thus, for example, reference to an antigenic fragment includes mixtures of antigenic fragments, reference to a pharmaceutical carrier or adjuvant includes mixtures of two or more such carriers or adjuvants.

As used herein, a subject is meant an individual. Thus, the subject can include domesticated animals, such as cats and dogs, livestock (e.g., cattle, horses, pigs, sheep, and goats), laboratory animals (e.g., mice, rabbits, rats, guinea pigs) and birds. In one aspect, the subject is a mammal such as a primate or a human.

Optional or optionally means that the subsequently described event or circumstance can or cannot occur, and that the description includes instances where the event or circumstance occurs and instances where it does not. For example, the phrase optionally the composition can comprise a combination means that the composition may comprise a combination of different molecules or may not include a combination such that the description includes both the combination and the absence of the combination (i.e., individual members of the combination).

Ranges may be expressed herein as from about one particular value, and/or to about another particular value. When such a range is expressed, another aspect includes from the one particular value and/or to the other particular value. Similarly, when values are expressed as approximations, by use of the antecedent about, it will be understood that the particular value forms another aspect. It will be further understood that the endpoints of each of the ranges are significant both in relation to the other endpoint, and independently of the other endpoint.

When the terms prevent, preventing, and prevention are used herein in connection with a given treatment for a given condition (e.g., preventing pneumococcal infection), they mean that the treated patient either does not develop a clinically observable level of the condition at all, or develops it more slowly and/or to a lesser degree than he/she would have absent the treatment. These terms are not limited solely to a situation in which the patient experiences no aspect of the condition whatsoever. For example, a treatment will be said to have prevented the condition if it is given during exposure of a patient to a stimulus that would have been expected to produce a given manifestation of the condition, and results in the patient's experiencing fewer and/or milder symptoms of the condition than otherwise expected. A treatment can prevent infection by resulting in the patient's displaying only mild overt symptoms of the infection; it does not imply that there must have been no penetration of any cell by the infecting microorganism.

Similarly, reduce, reducing, and reduction as used herein in connection with the risk of infection with a given treatment (e.g., reducing the risk of a pneumococcal infection) refers to a subject developing an infection more slowly or to a lesser degree as compared to a control or basal level of developing an infection in the absence of a treatment (e.g., administration of an immunogenic polypeptide). A reduction in the risk of infection may result the patient's displaying only mild overt symptoms of the infection or delayed symptoms of infection; it does not imply that there must have been no penetration of any cell by the infecting microorganism.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

A number of embodiments of the invention have been described. Nevertheless, it will be understood that various modifications may be made. Furthermore, when one characteristic or step is described it can be combined with any other characteristic or step herein even if the combination is not explicitly stated. Accordingly, other embodiments are within the scope of the claims.

EXAMPLES

Example 1

PcpA Elicits Protection Against Lung Infection and Fatal Sepsis

Materials and Methods.

Bacterial strains, medium, and growth conditions. *S. pneumoniae* strains TIGR4 and EF3030, and their derivatives, were used in this study. Pneumococci were grown at 37° C. in Todd-Hewitt broth with 0.5% yeast extract (THY) or on blood agar plates unless otherwise indicated. When appropriate, erythromycin was added to the medium at a concentration of 0.3 µg/ml. Clinical isolates of *S. pneumoniae* (Table 2) and isolates of major clonal groups (Table 3) were used.

TABLE 2

Clinical Isolates of *Streptococcus pneumoniae*

| Strain | Capsular type | PspA family | Origin | Reference |
|---|---|---|---|---|
| R6 | Non-encapsulated variant of D39 (type 2) | 1 | New York | (Belanger et al., *J. Bacteriol.* 186: 8164-71 (2004); Ottolenghi and Hotchkiss, *Science* 132: 1257-8 (1960) |
| TIGR4* | 4 | 2 | Norway | Ren et al., *Infect. Immun.* 71: 75-85 (2003); Roach et al., *PNAS* 102: 9577-82 (2005) |
| BG12730* | 6 | 2/3 | Gambia | Shaper et al., *Infect. Immun.* 72: 5031-40 (2004) |
| BG10752* | 9 | 1 | Alabama | This Study |
| TJ0893* | 14 | 2 | Mississippi | Wu et al., *J. Infect. Dis.* 175: 839-46 (1997) |
| V175* | 18 | 2 | Tennessee | Robinson et al., *J. Infect. Dis.* 183: 1501-7 (2001) |

TABLE 2-continued

Clinical Isolates of *Streptococcus pneumoniae*

| Strain | Capsular type | PspA family | Origin | Reference |
|---|---|---|---|---|
| L82013* | 19 | 2 | Alaska | Briles et al., *Infect. Immun.* 188: 339-48 (2003) |
| EF3030* | 19F | 1 | Sweden | Briles et al., *Infect. Immun.* 188: 339-48 (2003); Briles et al., *Infect. Immun.* 73: 6945-51 (2005); Johnston et al., *Infect. Immun.* 74: 1171-80 (2006) |
| EF9303* | 23F | Unknown | Sweden | Wu et al., *Microb. Pathog.* 23: 127-37 (1997) |
| L82016* | 6B | 1 | U.S.A. | Briles et al., *Infect. Immun.* 60: 111-6 (1992); Briles et al., *Infect. Immun.* 188: 339-48 (2003) |
| D-1091B* | 23 | 1 | Unknown | This Study |

*clinical strains that are not separated by more than 10 passages from the original patient isolate. R6 was derived from strain D39, which was a patient isolate in the 1920's.

TABLE 3

*Streptococcus pneumoniae* of major clonal groups

| Strain | Capsular type | Origin | Characteristics | Reference |
|---|---|---|---|---|
| MA-14 | 14 | UK | Worldwide Erm$^r$ clone; MLST sequence type 9 | (1) |
| MB-23F | 23F | UK | Unknown disease; MLST sequence type 81 | (1) |
| MC-6B | 6B | Spain | Unknown disease; MLST sequence type 90 | (3, 4) |
| MD-6B | 6B | Alaska | Unknown disease; MLST sequence type 138 | (2) |
| ME-19 | 19 | Tennessee | Carriage clone; MLST sequence type 236 | (2) |
| MF-6A | 6A | Tennessee | Carriage clone; Unknown MLST sequence type | (2) |
| MG-1 | 1 | UK | Major invasive clone; MLST sequence type 227 | (1) |
| MI-7F | 7F | Norway | Major invasive clone; MLST sequence type 191 | (1) |
| MJ-35 | 35 | Tennessee | Carriage clone; MLST sequence type 65 | (2) |
| MK-22 | 22 | Tennessee | Major invasive clone; Unknown MLST sequence type | (2) |
| ML-11 | 11 | Tennessee | Carriage clone; MLST sequence type 62 | (2) |
| MM-14 | 14 | Tennessee | Major invasive clone; MLST sequence type 124 | (2) |
| MN-23F | 23 | Tennessee | Carriage clone; MLST sequence type 37 | (2) |

(1). Enright, M. C., and B. G. Spratt. 1998. A multilocus sequence typing scheme for *Streptococcus pneumoniae*: identification of clones associated with serious invasive disease. Microbiology 144: 3049-60.
(2). Robinson, D. A., K. M. Edwards, K. B. Waites, D. E. Briles, M. J. Crain, and S. K. Hollingshead. 2001. Clones of *Streptococcus pneumoniae* Isolated from Nasopharyngeal Carriage and Invasive Disease in Young Children in Central Tennessee. J Infect Dis 183: 1501-7.
(3). Hakenbeck, R., T. Briese, L. Chalkley, H. Ellerbrok, R. Kalliokoski, C. Latorre, M. Leinonen, and C. Martin. 1991. Antigenic variation of penicillin- binding proteins from penicillin-resistant clinical strains of *Streptococcus pneumoniae*. J Infect Dis 164: 313-319.
(4). Hakenbeck, R., T. Briese, L. Chalkley, H. Ellerbrok, R. Kalliokoski, C. Latorre, M. Leinonen, and C. Martin. 1991. Variability of penicillin-binding proteins from penicillin-sensitive *Streptococcus pneumoniae*. J Infect Dis 164: 307-312.

The clinical strains used in these studies were isolated within the last 25 years. To examine the possible diversity of PcpA, isolates were selected from the group of strains utilized in the *Streptococcus pneumonia* Genome Diversity Project (http://genome.microbio.uab.edu/strep/info).

During strain construction, plasmids were maintained in *Escherichia coli* TOP10 cells (Invitrogen, Carlsbad, Calif.) grown in Luria-Bertani (LB) broth or LB plates with 1.5% agar. Ampicillin (50 µg/ml) for pCR2.1, pCR4 and pET-20b-based plasmids or erythromycin (400 µg/ml) for pJY4164-based plasmids was added to the growth medium.

THY medium was used for growth of bacteria in high manganese medium. For growth in low manganese conditions, a manganese depleted form of THY was prepared. THY medium was prepared according to the manufacturer's directions, with Chelex-100 (2% w/v) (Sigma Aldrich, St. Louis, Mo.) added prior to autoclaving. After autoclaving, the THY/Chelex mixture was stirred overnight at room temperature, followed by filter sterilization. $ZnCl_2$, $MgCl_2$, $CaCl_2$, and $FeSO_4$ were added to concentrations of 1 mM each, and $MnSO_4$ was add to a concentration of 0.1 µM prior to use. Growth was monitored by optical density at 600 nm.

Strain construction. The *E. coli* strains, plasmids, and primers used in this study are listed (Table 4). Mutagenesis was used to inactivate pcpA in the parental strains TIGR4 and EF3030. The construction of mutant strains was previously carried out and described (Johnston, et al., *Infect. Immun.* 74:1171-80 (2006)).

TABLE 4

Additional bacterial strains, and plasmids used in this study

| Strain, plasmid, or primer | Relevant characteristics or sequence and gene | Reference |
|---|---|---|
| Strains | | |
| *S. pneumoniae* | | |
| JEN7 | TIGR4 psaR::Erm (pcpA constituative mutant) | Johnston, et al., Infect. Immun. 74: 1171-80 (2006) |
| Jen11 | TIGR4pcpA::Erm | Johnston, et al., Infect. Immun. 74: 1171-80 (2006) |
| *E. coli* | | |
| TOP 10 | General cloning strain | Invitrogen, Carlsbad, CA |
| Rosetta (DE3) pLysS | Expression strain | Novagen, Madison, WI |
| Plasmids | | |
| pCR2.1 | 3.9 kb, Amp$^r$, Kan$^r$ | Invitrogen, Carlsbad, CA |
| pCR4 | 3.9 kb, Amp$^r$, Kan$^r$ | Invitrogen, Carlsbad, CA |
| pET-20b | 3.7 kb, Amp$^r$, C-term his-tag | Novagen, Madison, WI |
| pDG-1 | pCR4 with pcpA fragmnet; Amp$^r$ | This study |
| pJM-1 | pET-20b with pcpA fragment, Amp$^r$ | This study |
| pJJ035 | pCR2.1 with 412 bp internal pcpA fragment; Amp$^r$ | This study |
| Primers[a] | | |
| DTG-16 | cgcggatccATATGTCCCTAATGAACC (SEQ ID NO: 39); pcpA F | This study |
| DTG-12 | gcgctcgagTTCCTTTAATGAATCTAAGACGC CACTTAGGAAGAAGGAC (SEQ ID NO: 40); pcpA R | This study |
| JWJ28 | AAC TGT TCA AGT GGG TAA TGG (SEQ ID NO: 43); pcpA F | Johnston, et al., Infect. Immun. 74: 1171-80 (2006) |
| JWJ29 | TGA ACT TGA GGA AAA GGT TAG C (SEQ ID NO: 44); pcpA R | Johnston, et al., Infect. Immun. 74: 1171-80 (2006) |
| BGP1 | ATGAAAAAACTACAATATTATCATTAAC TACAGCTGCG (SEQ ID NO: 45); pcpA F | This study |
| BGP2 | CCATAAACCTTTGTCTTTAACCCAACCA ACTAC (SEQ ID NO: 46); pcpA R | This study |

[a]Primers were based on the complete genome sequence of *S. pneumoniae* TIGR4 (2). Lowercase denotes mismatches used to create restriction endonuclease sites. All sequences are expressed 5' to 3'.

Recombinant PcpA expression and purification. The strains, plasmids, and primers used in this study are listed in Table 2. Primers DTG-16 (5'-CGCGGATCCATATGTC-CCTAATGAACC-3' (SEQ ID NO:39)) and DTG-12 (5'-GCGCTCGAGTTCCTTTAATGAATCTAA-GACGCCACTTAGGAAGAAGGA C-3' (SEQ ID NO:40)) were designed to amplify a 1126 bp fragment of pcpA in strain TIGR4. The primers contain engineered restriction endonuclease sites, BamHI and XhoI respectively. Reactions were carried out for 30 cycles in a total volume of 50 µl in a cocktail containing 3.0 mM MgCl$_2$, 125 µM dNTPs, 50 picomole of each primer, and 2.5 units of Taq DNA Polymerase. The cycle was 94° C., 1 min.; 55° C., 1 min; 72° C., 5 minutes. This amplified gene fragment was initially cloned into pTOPO4 (Invitrogen, Inc., Carlsbad, Calif.) by a T-tailed method forming plasmid pLMG.

This fragment was cloned into pCR4 with the TOPO TA cloning kit (Invitrogen, Carlsbad, Calif.). Purified plasmids were screened by endonuclease digestion with BamHI and XhoI (Promega, Madison, Wis.). Agarose gel electrophoresis, PCR analysis, and DNA sequencing were all used to confirm insertion of the pcpA fragment in the resulting plasmid, pDG-1. The insert from pDG-1 was subcloned into the pET-20b expression vector (Novagen, Madison, Wis.). The resulting plasmid, pJM-1, was transformed into the *E. coli* strain RosettaBlue (DE3) pLysS (Novagen, Madison, Wis.) for protein production. This strain contains a chromosomal copy of the T7 promoter under control of the inducible UV5 promoter. Upon IPTG induction a truncated protein, containing amino acids 19-391, was expressed. The over-expressed truncated protein was purified using the Novagen HIS-BIND® Purification Kit (Novagen, Madison, Wis.), which utilized a C-carboxy terminal histidine tag to facilitate purification. Subsequent SDS-PAGE analysis with Comassie Blue staining yielded a single band of approximately 41-kDa.

Below is the complete sequence of the rPcpA protein that has been cloned and expressed. Underlined portions are from the cloning vector.

(SEQ ID NO: 41)
<u>MDIGINSDP</u>YVPNEPILADTPSSEVIKETKVGSIIQQNNIKYKVLTVEGN

IGTVQVGNGVTPVEFEAGQDGKPFTIPTKITVGDKVFTVTEVASQAFSYY

PDETGRIVYYPSSITIPSSIKKIQKKGFHGSKAKTIIFDKGSQLEKIEDR

AFDFSELEEIELPASLEYIGTSAFSFSQKLKKLTFSSSSKLELISHEAFA

NLSNLEKLTLPKSVKTLGSNLFRLTTSLKHVDVEEGNESFASVDGVLFSK

DKTQLIYYPSQKNDESYKTPKETKELASYSFNKNSYLKKLELNEGLEKIG

TFAFADAIKLEEISLPNSLETIERLAFYGNLELKELILPNNVKNFGKHVM

NGLPKLKSLTIGNNINSLPSFFLSGVLDSLKE<u>LEHHHHHH</u>

Anti-PcpA polyclonal antibody production. Purified rPcpA was used to immunize a New Zealand White Rabbit (Myrtle's Rabbitry, Thompson Station, Tenn.) rabbit subcutaneously to obtain anti-PcpA polyclonal serum. The rabbit was injected subcutaneously with 100 µg of rPcpA in 1 ml of Freund's complete adjuvant, 2 ml total volume. A second boost, with 100 µg of rPcpA in Freund's incomplete adjuvant, was given 2 weeks later and a third boost of 100 µg of PcpA in Freund's incomplete adjuvant was given 2 weeks after the second boost. Two weeks following the final boost the rabbit was bled by cardiac puncture, under anesthesia. The blood was allowed to clot, and serum was obtained by centrifugation and stored at −80° C.

PCR confirmation of pcpA in *S. pneumoniae* strains. The presence or absence of pcpA in various *S. pneumoniae* strains was checked using PCR primer pair BGP-1 and BGP-2. The primer pair was designed to amplify a 1416 bp N-terminal fragment of pcpA in strain TIGR4. The PCR products were then separated on a T.A.E. agarose gel, stained with ethidium bromide, and examined for the correct size amplified band.

*S. pneumoniae* cell fractionation. Protoplasts were produced with the method described by Yother and White (Yother and White, *J. Bacteriol.* 176:2976-85 (1994)), with slight modification. Log-phase cells, grown in MTHY, were pelleted and washed in PBS. The cells were then resuspended in 0.5 ml of 2% choline chloride and the tube inverted several times. The cells were then pelleted and the supernatant drawn off and stored at −20° C. (choline elution fraction). Cells were pelleted and washed once with 300 µl of protoplast buffer (20% sucrose, 5 mM Tris [pH 7.4], 2.5 mM MgSO$_4$). The pellet was then resuspended in 1 ml protoplast buffer, and Mutanolysin (Sigma Aldrich, St. Louis, Mo.) was then added at 5 Upper ml of culture pelleted. The suspension was incubated overnight at room temperature. Cells were pelleted by centrifugation at 6000 rpm for 10 min, supernatant is stored at −20° C. (Cell Wall Fraction). The protoplast were then washed in 1 ml of protoplast buffer. The formation of protoplasts was confirmed by microscopic examination. The protoplast were pelleted and lysed in 0.3-1 ml of dH$_2$O, this is stored at −20° C. (Cell Membrane/Cytosolic Fraction). Samples of each fraction are examined for the presence of PcpA by Western blot analysis.

Antibody staining of *S. pneumoniae*. Mid-log-phase cells, OD$_{600}$ 0.6, grown in high or low manganese medium, were pelleted, washed with PBS, resuspended in PBS with 1% bovine serum albumin (PBSB), and incubated at room temperature 20 min. Cells were pelleted and resuspended in PBSB or anti-PcpA serum diluted 1:100 in PBSB and incubated at 37° C. for 30 min. Incubation was followed by two washes with PBS. Cells were then incubated with goat anti-rabbit immunoglobulin G (heavy and light chains)-fluorescein isothiocyanate (Southern Biotechnology Associates, Inc., Birmingham, Ala.) diluted in PBSB at 4° C. for 30 min. The cells were then washed twice with PBS and resuspended in 4% formaldehyde in PBS containing 0.01 mM of the lipophylic membrane dye TMA-DPH (Invitrogen, Carlsbad, Calif.). Bacterial cells were then inspected by epifluorescence using the Olympus IX 70 microscope.

Western blot. Bacterial cultures were grown in THY and MTHY to mid-log phase, OD$_{600}$ 0.6. Equivalent amounts of each strain were washed twice with phosphate-buffered saline (PBS), resuspended in PBS with sodium dodecyl sulfate-polyacrylamide gel electrophoresis (SDS-PAGE) sample buffer, and boiled for 5 min. Samples and a prestained protein standard (Invitrogen, Carlsbad, Calif.) were loaded onto a NuPAGE 10% Bis-Tris gel (Invitrogen, Carlsbad, Calif.) and separated by electrophoresis in morpholineethanesulfonic acid (MES)-SDS running buffer (Invitrogen, Carlsbad, Calif.) in accordance to the manufacturer's instructions. Proteins were then transferred to a nitrocellulose membrane with the Trans-Blot SD semidry transfer cell (Bio-Rad, Hercules, Calif.). The blot was probed with anti-PcpA polyclonal antibody diluted 1:1000 in PBSB. Goat anti-rabbit immunoglobulin G (heavy and light chains)-alkaline phosphatase and streptavidin-alkaline phosphatase (Southern Biotechnology Associates, Inc., Birmingham, Ala.) were used as the secondary antibody. Colorimetric detection was performed with Sigma Fast nitrobluetetrazolium-5-bromo-4-chloro-3-indolylphosphate (NBT-BCIP) tablets (Sigma Aldrich, Switzerland).

Systemic immunization of mice. 6-8 week old CBA/CaH-NBtkxid/J (CBA/N) mice (JacksonLabs, Bar Harbor, Me.) were initially injected subcutaneously with 10 µg of rPcpA with 2 µg of Aluminum hydroxide as an adjuvant, 200 µl total volume. A second boost with 10 µg of rPcpA with Aluminum hydroxide was given 2 weeks later. A third boost containing 10 µg of rPcpA without Aluminum hydroxide was given 2 weeks following. The mice were then allowed to rest 2 weeks prior to challenge with *S. pneumoniae*. Mice were bled 24 hrs prior to infection.

Murine model of sepsis. The virulence of pneumococci was examined in a systemic model of infection previously described (Coats, et al., *Vaccine* 23:4257-62 (2005); Ren et al., *Infect. Immun.* 71:75-85 (2003)). 6-8 week old CBA/N mice were injected intravenously with 300 CFUs of bacteria diluted in lactated ringers. Mice were monitored for 21 days. When they become unresponsive to touch and their body temperature decreased to below normal they were scored as moribund and the date and time were recorded. All moribund mice were euthanized with CO$_2$ narcosis.

Murine model of pneumonia. Lung infections were performed as previously described (Balachandran et al., *Infect. Immun.* 70:2526-34 (2002); Briles et al., *J. Infect. Dis.* 188:339-48 (2003); Takashima et al., *Infect. Immun.* 65:257-260 (1997)). 6-8 week old CBA/N mice were anesthetized with Isoflurane (MinRAD, Buffalo, N.Y.), and suspensions of 40 µl of lactated ringers solution containing 5×10$^6$ bacteria were introduced into the nares of the mice to induce aspiration pneumonia. After 7 days the mice were sacrificed. The nasal cavities of sacrificed mice were washed with 50 µl of lactated ringers, as previously described (Wu et al., *J. Infect. Dis.* 175:839-46 (1997)). The nasal wash was serially diluted and plated onto blood agar with gentamicin (4 µg/ml). The lungs were harvested and placed into 2 ml of lactated ringers in a stomacher bag, homogenized, serially diluted, and plated onto blood agar with gentamicin in serial 3-fold dilutions.

Murine model of nasopharyngeal colonization: Intranasal inoculations were performed as previously described (Balachandran et al., *Infect. Immun.* 70:2526-34 (2002); Wu et al., *J. Infect. Dis.* 175:839-46 (1997)). 6-8 week old CBA/N mice were infected intranasally with 10$^6$ bacteria in 10 µl of lactated Ringer's solution without anesthesia. Infected mice were then sacrificed, and their nasal cavities were washed with 50 µl of Ringer's solution. The nasal washes were serially diluted and plated on blood agar with gentamicin. Visible counts from blood agar plates were determined after overnight incubation at 37° C. in candle jars.

Statistical analysis. Statistically analysis was carried out using Instat (GraphPad Software Inc., San Diego, Calif.). Comparisons of time to moribund or numbers of recovered CFU between the control and experimental groups were conducted using the Mann-Whitney two sample rank test. P-values less than 0.05 were considered to be statistically significant.

Results pcpA is present in clinically relevant strains of *S. pneumoniae*. The presence of pcpA was examined by PCR, with primers (BGP1 and BGP2) spanning the LRR region of the pcpA. Each of the 23 strains examined (Tables 2 and 3) yielded a roughly 1500-bp fragment. Eight of these strains are clinical strains isolated within the last 25 years that are representative strains of the seven common capsular types covered by the 7-valent conjugate vaccine (FIG. 1). The remaining 12 strains are a set of *S. pneumoniae* that were selected from a set of strains assembled as part of the Genome Diversity Project (http://genome.microbio.uab.edu/strep/info/) which includes a set of strains chosen to span the breadth of diversity in *S. pneumoniae*. These 12 strains were selected as highly divergent based on MLST data. Four strains were from patients with serious invasive disease, five were from asymptomatic carriage, for 2 strains disease/colonization was not know, and one strain was from a worldwide antibiotic resistant clone. These strains represent 12 different capsule types from different world regions.

Figure 2:
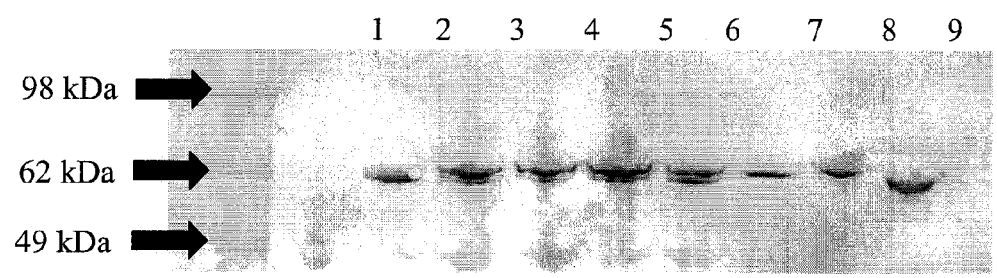
FIG. 2 shows Western blot analysis of PcpA presence under low Mn2+ conditions. Bacteria were cultured in low Mn2+ medium until mid-log phase and total cellular protein samples prepared. Samples were separated by SDS-PAGE, transferred to nitrocellulose and probe with a rPcpA polyclonal antiserum. Lane 1, JEN11 (pcpA– mutant); Lane 2, JEN7 (pcpA constitutive mutant); Lane 3, D1091B; Lane 4, EF5668; Lane 5, BG10752; Lane 6, V175; Lane 7, L82013; Lane 8, BG12730; Lane 9, TJ0893.

To test for expression of PcpA in all strains they were grown in low ($\leqq 0.1$ μM) manganese. Total cellular protein samples were prepared from mid-log phase cells cultured in the low manganese medium. All strains listed in (Tables 2 and 3) were examined, but only those representing capsular types included in the heptavalent vaccine are depicted (FIG. 2). Total cellular protein samples were separated by SDS-PAGE and transferred to nitrocellulose. The blot was probed with anti-PcpA polyclonal antiserum, identifying a band of approximately 62-kDa in each of these wild-type strains of capsulare serotypes 4, 6, 9, 14, 18, 19, 23 (FIG. 2). This 62-kDa band was absent in the pcpA-inactivated mutant JEN11 but was present in seven representative strains. Total cellular protein samples were also prepared from strains grown in high manganese medium for the same strains, but no bands were identified with the anti-PcpA antiserum. The PCR analysis in combination with the Western blot data, demonstrated that pcpA is present in all *S. pneumoniae* strains listed in Tables 2 and 3.

PcpA is exposed on the surface of *S. pneumoniae* under low manganese conditions. Studies have shown that through the action of the regulator PsaR, manganese controls the transcription of the pcpA gene (Johnston et al., *Infect. Immun.* 74:1171-80 (2006)). As described herein, manganese dependent regulation directly affects the presence of PcpA on surface of *S. pneumoniae* and surface PcpA is accessible to antibody even on encapsulated pneumococci.

Cell fractionation was performed to determine if PcpA was associated with the cell wall or cell membrane/cytosol of *S. pneumonia*. Western blot analysis of these cellular fractions revealed that PcpA was present predominantly in the cell wall of *S. pneumoniae*, in bacteria grown in low manganese medium. A small fraction of the PcpA was associated with the cell membrane/cytosol, and probably represents PcpA yet to be exported to the surface of the bacteria.

In addition to the cell fractionation, log-phase cells from wild type *S. pneumoniae* strain TIGR4 were grown in high or low manganese medium, stained with anti-PcpA polyclonal antiserum followed by fluorescein isothiocyanate (FITC)-conjugated anti-rabbit immunoglobulin. Specifically, TIGR4 was cultured in high or low Mn2+ medium until mid-log phase. Bacteria were incubated with anti-PcpA rabbit serum, followed by incubation with FITC-conjugated anti-rabbit Ig antibodies. Cells were then fixed in 4% formaldehyde containing the membrane dye TMA-DPH. The labeled bacteria were then examined by immunofluorescence microscopy. The antibodies to PcpA were able to mediate staining of the bacteria grown in low manganese, but not those grown in high manganese.

These results indicate that PcpA is surface exposed on wild-type *S. pneumoniae* cultured under low manganese conditions in vitro. This indicates that PcpA is expressed and surfaced exposed on bacteria infecting low manganese sites inside the host, such as the lungs and blood. This exposure of PcpA facilitates PcpA-ligand interactions between the bacterium and the host epithelium during infection. These results also indicate that regulation of PcpA production by manganese concentration is generalizable to most pneumococci.

Immunization with rPcpA elicits antibody and provides protection against lung and systemic infection, but does not significantly affect nasopharyngeal colonization. Mice were immunized with rPcpA with aluminum hydroxide or received aluminum hydroxide alone, prior to use in infection studies. Total Ig(H+L) was quantified for both groups of mice by ELISA. The geometric mean level of antibody specific PcpA in the serum of the immunized mice was 0.465 (±0.119) μg/ml, versus a mean of 0.002 (±0.002) μg/ml for mice receiving the adjuvant alone, (±SEM). This indicates the route of immunization was successful at eliciting an immune response to rPcpA.

Figure 3A:
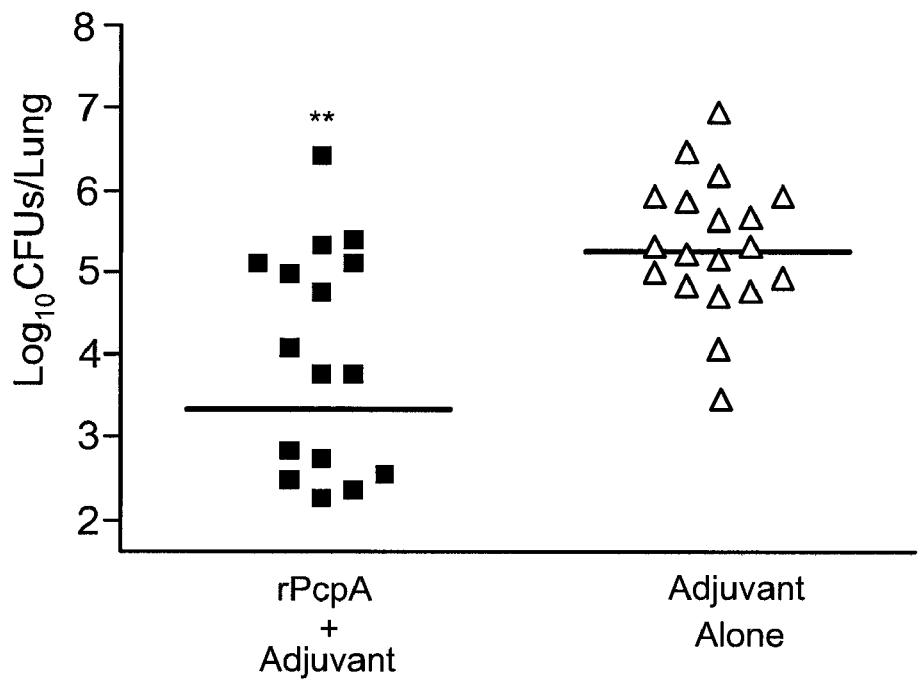
FIG. 3 shows that protection against lung infection but not against nasal colonization conferred by rPcpA immunization compared to adjuvant alone was statistically significant in a murine model of pneumonia. CBA/N mice were subcutaneously immunized with rPcpA adsorbed to aluminum hydroxide or aluminum hydroxide alone. Mice were challenged intranasally under light anesthesia, with $5 \times 10^6$ CFUs of EF3030. Mice were sacrificed 7 days post-infection and bacterial counts determined from lung homogenates (FIG. 3A) and nasal washes (FIG. 3B). Horizontal line denotes median Log 10 CFUs. (**:p=0.0019, Mann-Whitney).
Figure 3B:
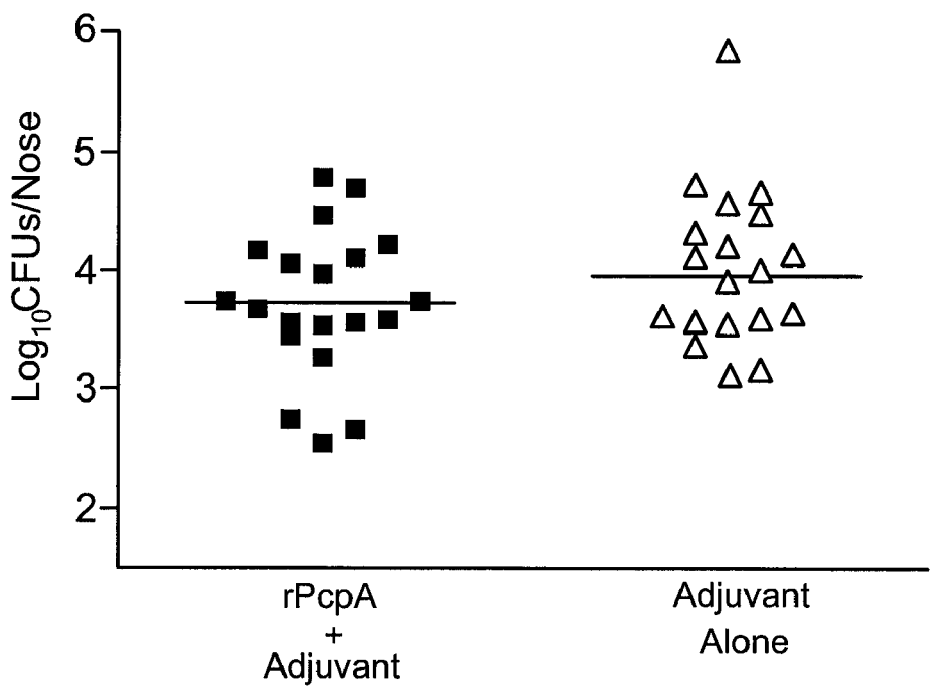
Figure 4A:
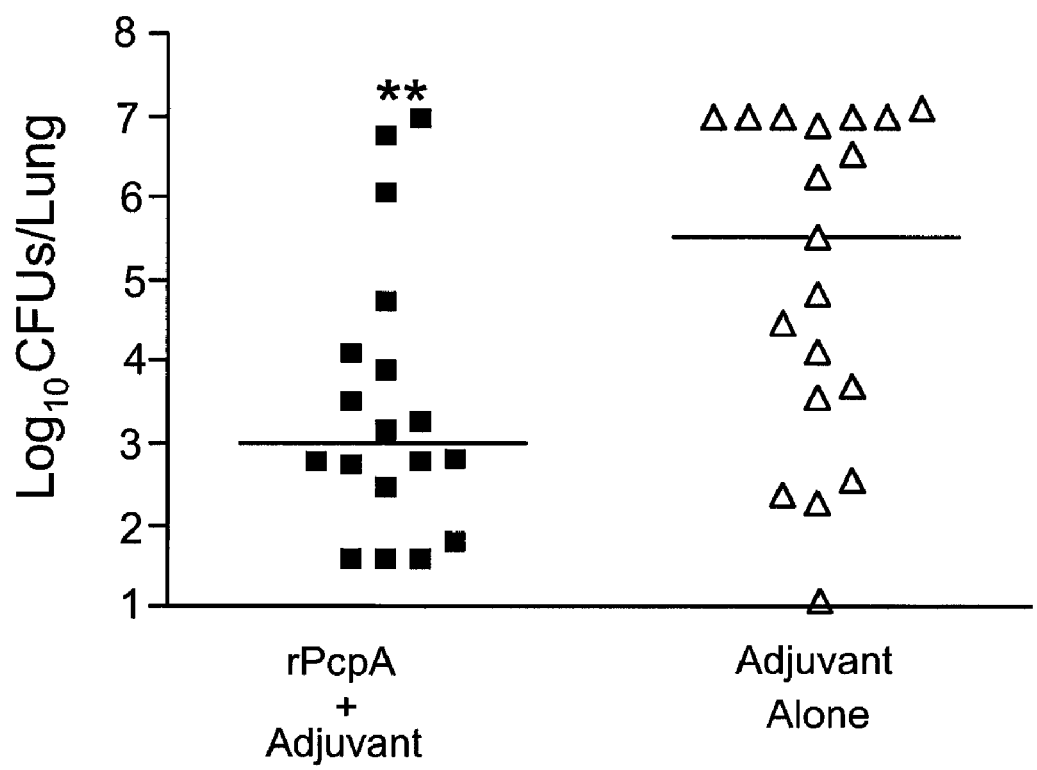
FIG. 4 shows that protection conferred against other *S. pneumoniae* capsular serotypes by rPcpA immunization versus adjuvant alone was statistically significant in a murine model of pneumonia. Mice were challenged with strains (FIG. 4A) TJ0893, serotype 14 (:p=0.0209)
(FIG. 4B) L82016, serotype 6B (:p=0.0193)
(FIG. 4C) EF9303, serotype 23F (**:p=0.0388, Mann-Whitney). Horizontal line denotes median Log 10 CFUs.
Figure 4B:
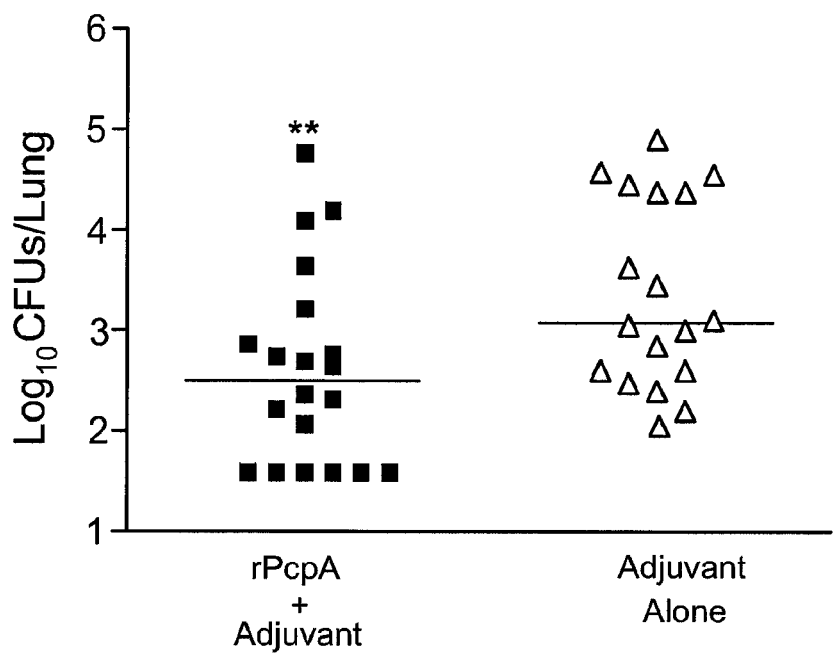
Figure 4C:
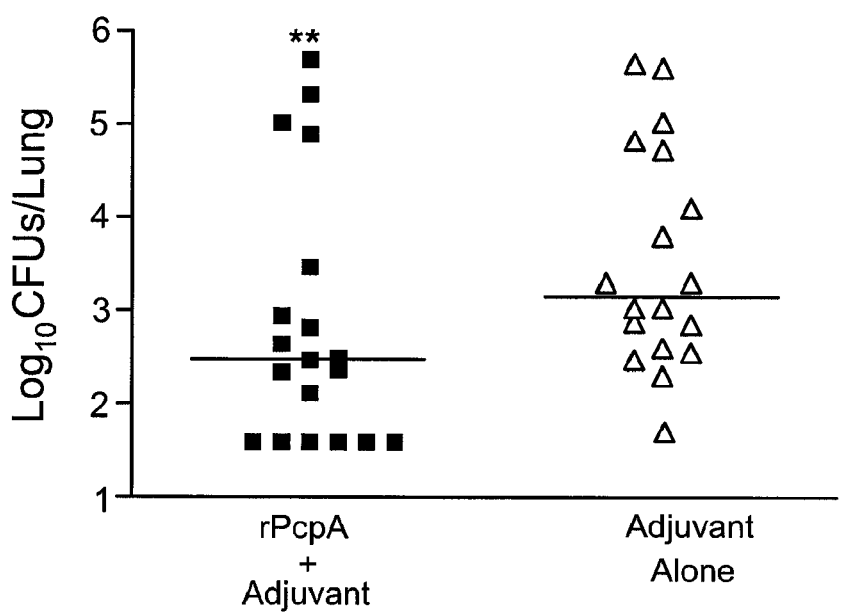

To see if the immunization protected mice from pneumonia, the immunized and alum-only mice were lightly anesthetized and inoculated in the nares with $5 \times 10^6$ CFU of strain EF3030. This procedure resulted in focal pneumonia without bacteremia. Protection in this model can thus be associated with pneumonia per se and not sepsis in general. Seven days post infection all mice were sacrificed. Bacterial counts were determined from homogenized lung tissue and nasal wash. Based on the median CFU recovered, there were less than 1/100 as many pneumococci recovered from the lung homogenates of mice immunized with rPcpA versus those receiving adjuvant alone (FIG. 3A) (P=0.002). These results indicate that immunization with rPcpA is able to elicit protection against pulmonary infection with *S. pneumoniae*. There was no significant difference in the bacterial counts recovered from nasal washes of mice immunized with rPcpA versus those receiving adjuvant alone (FIG. 3B).

Figure 5:
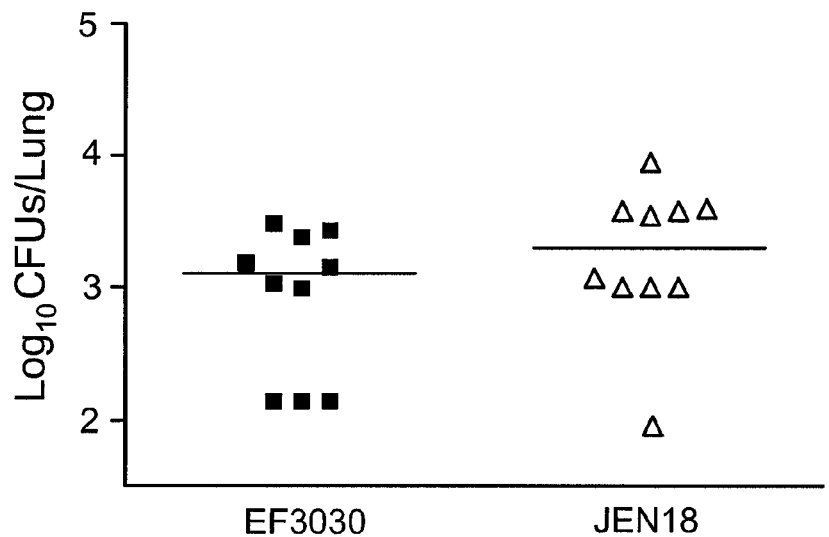
FIG. 5 shows the lack of an effect of pcpA inactivation on intranasal colonization of *S. pneumoniae*. Mice were challenged intranasally with $10^6$ CFUs of EF3030 or its derivative JEN18. Mice were sacrificed 7 days post-infection and bacterial counts determined from nasal washes. Horizontal line denotes median Log 10 CFUs/Nose.

Next it was determined whether subcutaneous immunization would confer protection against focal lung infection with other strains of *S. pneumoniae* (TJ0893, serotype 14; EF9303, serotype 23F; and L82016, serotype 6B). Subcutaneous immunization with rPcpA elicited significant protection against each strain compared to mice receiving immunizations of just the adjuvant alone (FIG. 5).

Expression of PcpA is not required for optimal nasal colonization. Since immunization did not affect the number of bacteria recovered from the nasal washes of mice used for the pneumonia model, the effect of pcpA inactivation was examined in a model of nasopharyngeal carriage. This model allowed a direct view of any effects of PcpA on nasal carriage, as opposed to the indirect observations gathered from the nasal washes of mice in the pneumonia model. Mice were inoculated without prior anesthesia with $10^6$ CFU of either strain EF3030 or its pcpA-inactivated mutant JEN18. Seven days post infection the mice were sacrificed and nasal washes were collected and plated to detect pneumococci. There was no significant difference in the number of bacteria recovered from the nasal washes of mice inoculated with either EF3030 or JEN18 (FIG. 5).

The failure of either the presence of an intact pcpA gene or subcutaneous immunization with rPcpA to have an effect on numbers of pneumococci recovered in the nasal washes of mice is consistent with the fact that the manganese concentration in the nasopharynx ($\geqq 36$ μM) is high enough to suppress pcpA transcription. Under these conditions pcpA transcription would be repressed, by psaR, in the nasopharynx.

Thus, immunity to PcpA would be expected to have little effect on bacteria in this host site.

Figure 6:
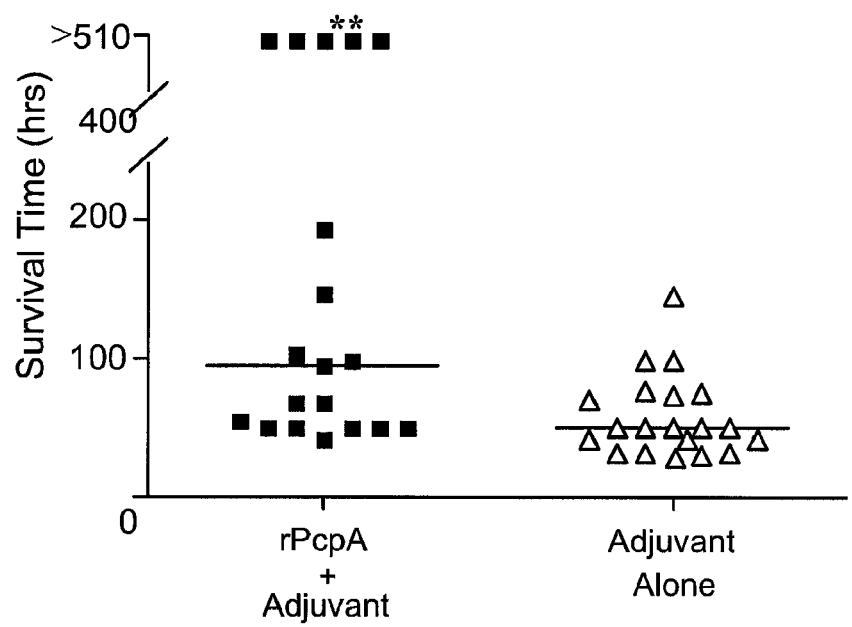
FIG. 6 shows that protection conferred by rPcpA immunization versus adjuvant alone was statistically significant in a murine model of fatal sepsis. CBA/N mice were subcutaneously immunized with rPcpA adsorbed to aluminum hydroxide or aluminum hydroxide alone. Mice were challenged intravenously with 300 CFUs of TIGR4 and survival time was monitored for 21 days. Horizontal line denotes median survival time. (**:P=0.0067, Mann-Whitney). Surviving mice were euthanized and, upon examination, none had detectable *S. pneumoniae* in their blood.

PcpA and immunity to PcpA effects virulence in the murine model of systemic infection. To evaluate the ability of immunity to PcpA to protect against sepsis, CBA/N mice were subcutaneously immunized with PcpA in aluminum hydroxide or aluminum hydroxide alone as a control and challenged intravenously with capsular type 4, TIGR4 S. pneumoniae. This strain was used rather than EF3030 since this strain can readily cause bacteremia and sepsis in mice. The immunized animals were injected IV with 300 CFU of TIGR4 strain S. pneumoniae. Survival was monitored for 21 days. Mice receiving rPcpA immunizations had a median time to become moribund that was extended by 43.5 hours compared to mice receiving adjuvant alone (FIG. 6). Twenty six percent of mice immunized with rPcpA lived, whereas no mice immunized with aluminum hydroxide alone lived; this difference in survival was statistically significant (P=0.007).

Figure 7:
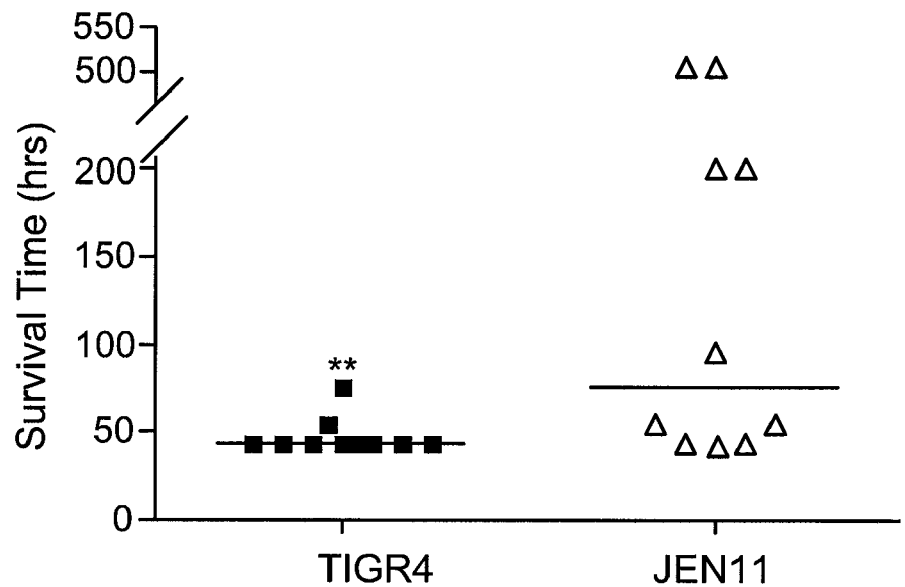
FIG. 7 shows virulence of TIGR4 and its pcpA inactivated derivative JEN11 in a murine model of sepsis. Mice were challenged intravenously with 300 CFUs of TIGR4 or JEN11 and survival time was monitored for 21 days. Horizontal line denotes median survival time. (**:P=0.0299, Mann-Whitney).

Effect of inactivation of pcpA on the ability of pneumococci to cause mice to become moribund following intravenous inoculation. Inactivation of pcpA results in reduced virulence in the murine model of pneumonia and in a lung-sepsis model. As described herein, the effect of pcpA inactivation on systemic infection following intravenous challenge was examined by infecting naive mice with 300 CFU of either TIGR4 or its pcpA inactivated mutant JEN11. The median time to become moribund for mice infected with the pcpA⁻ mutant was extended by 31.5 hours (P=0.0299) compared to those infected with wild-type bacteria (FIG. 7). This demonstrates that there is a role for PcpA in the ability of S. pneumoniae to cause systemic diseases.

Example 2

Mucosal Immunization with PcpA Protects Against Lung Infection

Figure 8:
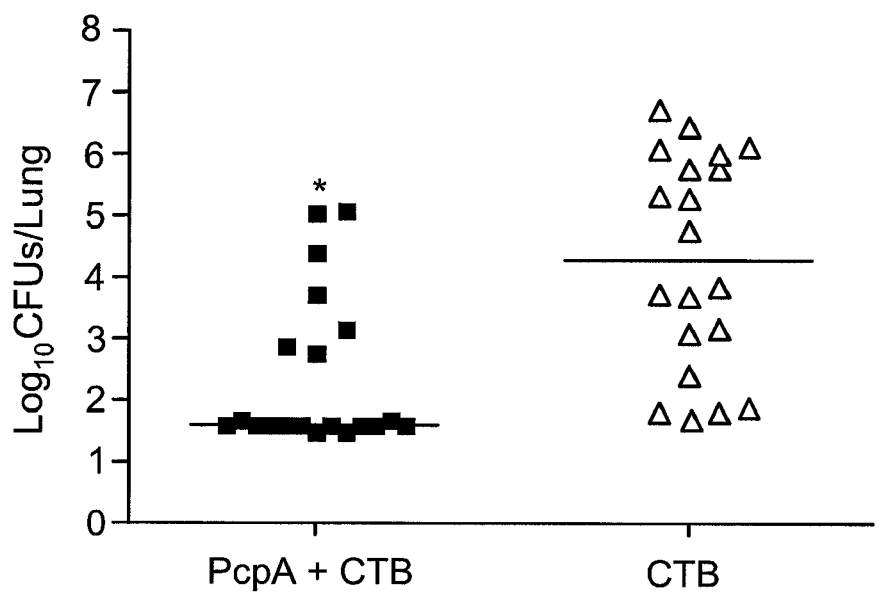
FIG. 8 shows that protection was conferred by rPcpA mucosal immunization compared to adjuvant alone in a murine model of pneumonia. CBA/N mice were intranasally immunized with rPcpA and cholera toxin B subunit (CTB) or CTB alone. Mice were challenged intranasally under light anesthesia, with $5\times10^6$ CFUs of EF3030. Mice were sacrificed 7 days post-infection and bacterial counts in the homogenized lungs were determined Horizontal line denotes median Log 10 CFUs. (*:P=0.0001, Mann-Whitney).

As shown in FIG. 8, mucosal immunization with PcpA protects against pulmonary infection with strain EF3030. CBA/N mice were immunized intranasally with 5 µg of PcpA plus cholera toxin B sub-unit (CTB) as the adjuvant. Post-immunization mice were bled and then challenged intranasally with 5×10⁶ CFU of strain EF3030. FIG. 8 shows log CFU of bacteria in lung homogenate at 7 days post-infection.

Mucosal immunization protection was observed to be slightly better than with immunization. These data and Example 1 indicate that protection against pneumonia and sepsis can be conferred using at least mucosal or subcutaneous routes of administration. Mucosal immunization with PcpA does not protect against nasal colonization with this strain. This is expected since PcpA is not expressed during colonization.

Example 3

Antibody Elicited by Subcutaneous or Intranasal Immunization with PcpA

Sera obtained from mice immunized with PcpA were examined for the level of antibody to PcpA. CBA/N mice were immunized either subcutaneously (SC) with aluminum hydroxide or cholera toxin B subunit (CTB) as the adjuvant on days 0 and 14, and with PcpA alone on day 21. On day 35 mice were bled and the antibody levels in the serum were determined by using as a standard the OD observed with a known concentrations of PspA antibodies reacting with PspA-coated microtitration plates. As controls, additional groups of mice were immunized with diluent and adjuvant alone. A 1.3-fold higher IgG antibody response was observed with SC rather than intranasal (IN) immunization (Table 5).

TABLE 5

| | | Antibodies to PcpA in mice immunized with PcpA | | | | |
|---|---|---|---|---|---|---|
| rPcpA Route of Admin. | Group | Ig (H + L) | IgG1 | IgG2a | IgG2b | IgA |
| | | | | Mean µg/ml (± SEM) | | |
| S.C. | rPcpA + Adjuvant (n = 10) | 0.465 (0.159) | 1.768 (0.378) | 0.123 (0.041) | 0.125 (0.048) | <0.001 |
| S.C. | Adjuvant alone (n = 10) | 0.002 (0.002) | 0.007 (0.007) | <0.001 | 0.002 (0.001) | <0.001 |
| I.N. | rPcpA + Adjuvant (n = 10) | 0.356 (0.159) | 0.151 (0.085) | 0.118 (0.057) | 0.093 (0.033) | <0.001 |
| I.N. | Adjuvant alone (n = 10) | <0.001 | <0.001 | <0.001 | <0.001 | <0.001 |

As is common with this type of assay, the amounts of the subclasses did not add up to the amount of total Ig. This is an indication that anti-IgG serum does not recognize all IgG subclasses equally.

Example 4

PcpA is Necessary for Adherence to Lung Cells

Figure 9:
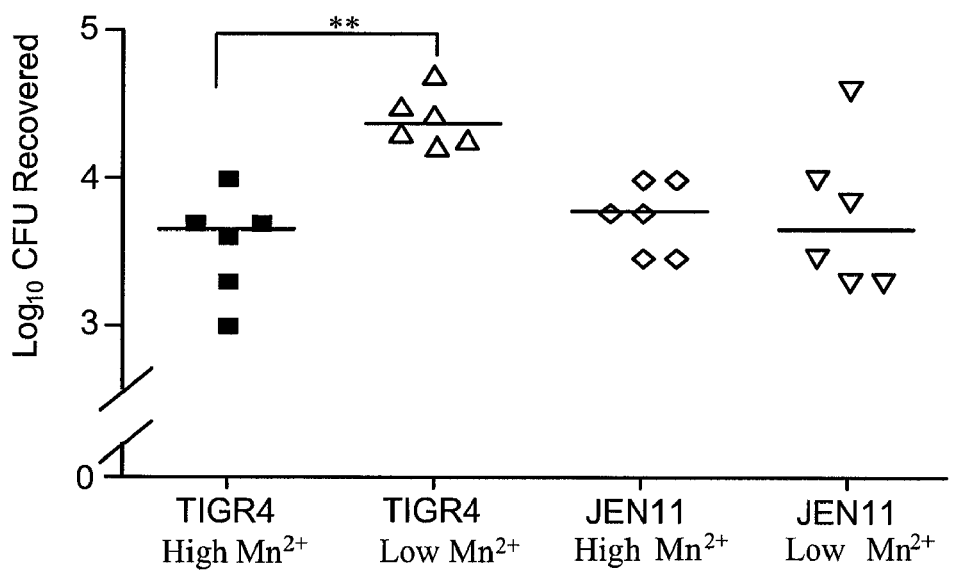
FIG. 9 shows adherence of pcpA+ and pcpA− TIGR4 strains (TIGR4 and JEN11, respectively) to human lung epithelial cells. A549 human lung epithelial cell monolayers were incubated for 150 minutes with $10^6$ CFU of pcpA+ and pcpA− TIGR4 strains that had been grown under high manganese (High $Mn^{2+}$) or low manganese (Low $Mn^{2+}$) growth conditions. The epithelial cells were washed and lysed. Numbers of adherent pneumococci in each lysate were determined by quantitative plating on blood agar plates. Log 10 CFU recovered refers to the number of pneumococci associated with the lung epithelial cells at the end of the experiment. (**:P=0.0022, Mann-Whitney).
Figure 10:
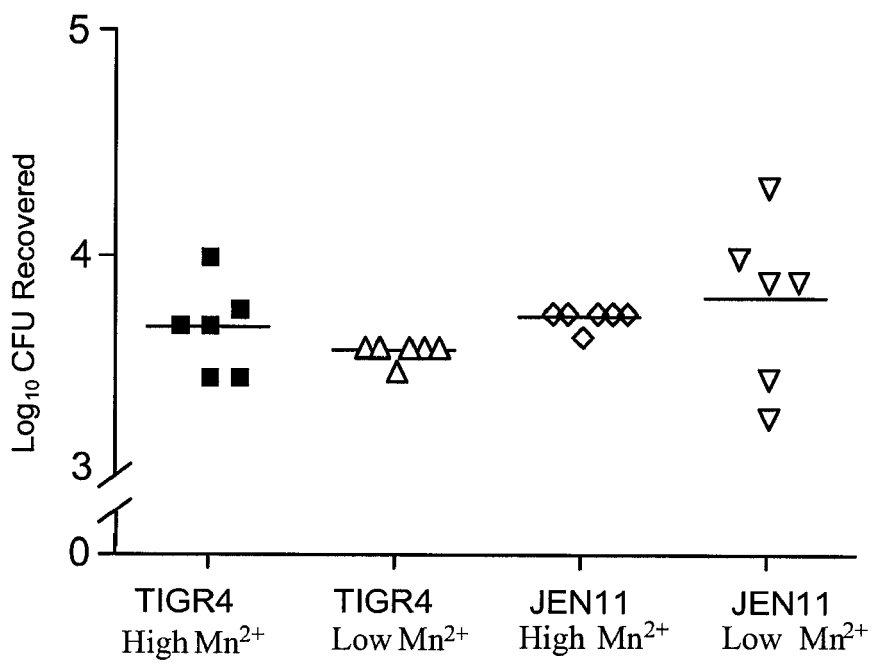
FIG. 10 shows pcpA+ and pcpA− TIGR4 strains did not adhere to human nasal epithelial cells. Detroit562 human nasal epithelial cell monolayers were incubated for 150 minutes with $10^6$ CFU of pcpA+ and pcpA− TIGR4 strains that had been grown under high manganese (High $Mn^{2+}$) or low manganese (Low $Mn^{2+}$) growth conditions. The cells were then washed and lysed. Numbers of pneumococci in the lysate were determined by quantitative plating on blood agar plates. Log 10 CFU recovered refers to the number of pneumococci at the end of the experiment.

PcpA is necessary for adherence to the A549 cell line of transformed lung epithelial cells (FIG. 9) but not to the Detroit562 line of transformed human nasal epithelial cell (FIG. 10). It was observed that adherence to the A549 lung epithelial cells also required that the pneumococci be grown in low $Mn^{2+}$ so that they would produce PcpA. The pneumococci for these studies were grown in Todd-Hewitt and Yeast medium (high $Mn^{2+}$) or Todd-Hewitt and Yeast Medium that had been passed over Chelex-100 (Sigma) and reconstituted with 0.1 µm $MnSO_4$ and 1 mM $ZnCl_2$, $MgCl_2$, $CaCl_2$, and $FeSO_4$. (low $Mn^{2+}$) (Briles et al., J. Infect. Dis. 188:339-48 (2003)). The Detroit 562 or A549 cells monolayers were incubated for 150 minutes with 10⁶ CFU of TIGR4 (pcpA+) or JEN11 (pcpA− TIGR4 strain). The epithelial cells with adherent bacteria were washed and lysed with 0.5% Tween 20. The numbers of pneumococci in the lysate were determined by quantitative plating on blood agar plates.

Figure 11:
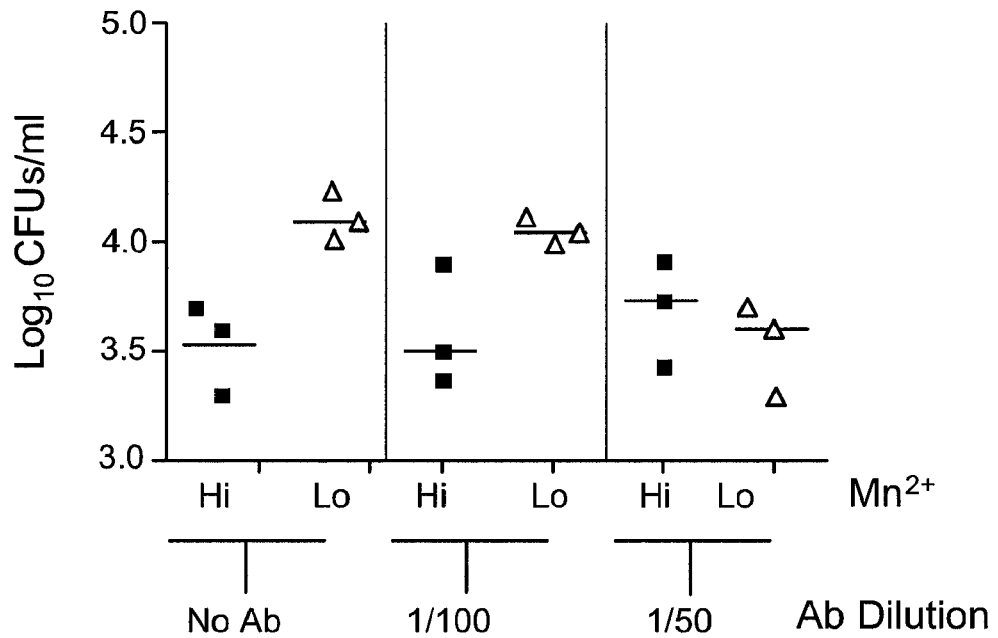
FIG. 11 shows inhibition of adherence of pneumococci to A549 cells by an antibody to PcpA. A549 human lung epithelial cell monolayers were incubated with $10^6$ CFU of pcpA+ and pcpA− TIGR4 strains grown in high manganese (High $Mn^{2+}$) or low manganese (Low $Mn^{2+}$) without antibody, with 1/100 dilution, or with 1/50 dilution of PcpA antibody. The cells were washed and lysed. Numbers of pneumococci in the lysate were determined by quantitative plating on blood agar plates.

Adherence of pneumococci to A549 cells is inhibited with antibody to PcpA (FIG. 11). These data demonstrate PcpA-dependent adherence of pneumococci to lung epithelial cells.

Example 5

Passive Protection Model

Figure 12:
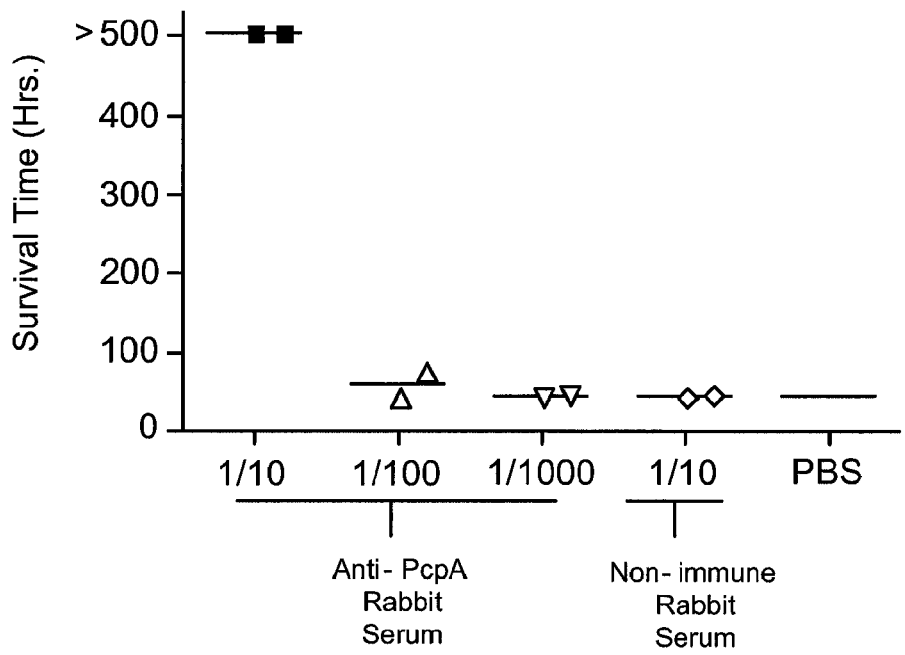
FIG. 12 shows protection against sepsis using rabbit sera to PcpA. Rabbit serum was prepared by immunizing a rabbit with 100 µg rPcpA in complete Freund's adjuvant followed two and four weeks later by 100 µg rPcpA in complete Freund's adjuvant. Sera was collected two weeks after the final boost and was shown to contain antibody to PcpA by dot blot assay. Pre-immune sera was also collected before the start of the immunizations. Mice were tested in groups of two for the ability of dilutions of the rabbit anti-sera to protect against fatal pneumococcal infection. Three groups of mice received 0.1 mL of 1/10, 1/100 or 1/1000 dilutions of the immune sera intraperitoneally one hour prior to i.v. challenge with TIGR4. Two mice received 1/10 pre-immune (non-immune) rabbit serum and two mice received the diluent, PBS, only. Mice were observed for 500 hours or until time of death. The two mice receiving 1/10 immune sera lived throughout the experiment. All other mice died between 40 and 60 hours post challenge.

Based on the ability of active immunization with PcpA to elicit protection against lung infection, it was determined whether antibody to PcpA would be able to passively protect mice from lung infection. However, passive protection has not yet been observed in a pneumonia model. In a second passive immunization study, passive protection against IV sepsis with the TIGR4 strain was determined using immune rabbit sera to PcpA. It was observed that the highest concentration of sera tested (1/10) was able to protect two of mice from death (FIG. 12). A non-immune serum was not able to protect at the same concentration. These data suggest that passive immunization can protect against TIGR4 strain, which can be a difficult strain to protect against (Roche et al., *Infect. Immun.* 71:4498-505 (2003)).

Example 6

Protection by PcpA and Pneumolysin

Figure 13:
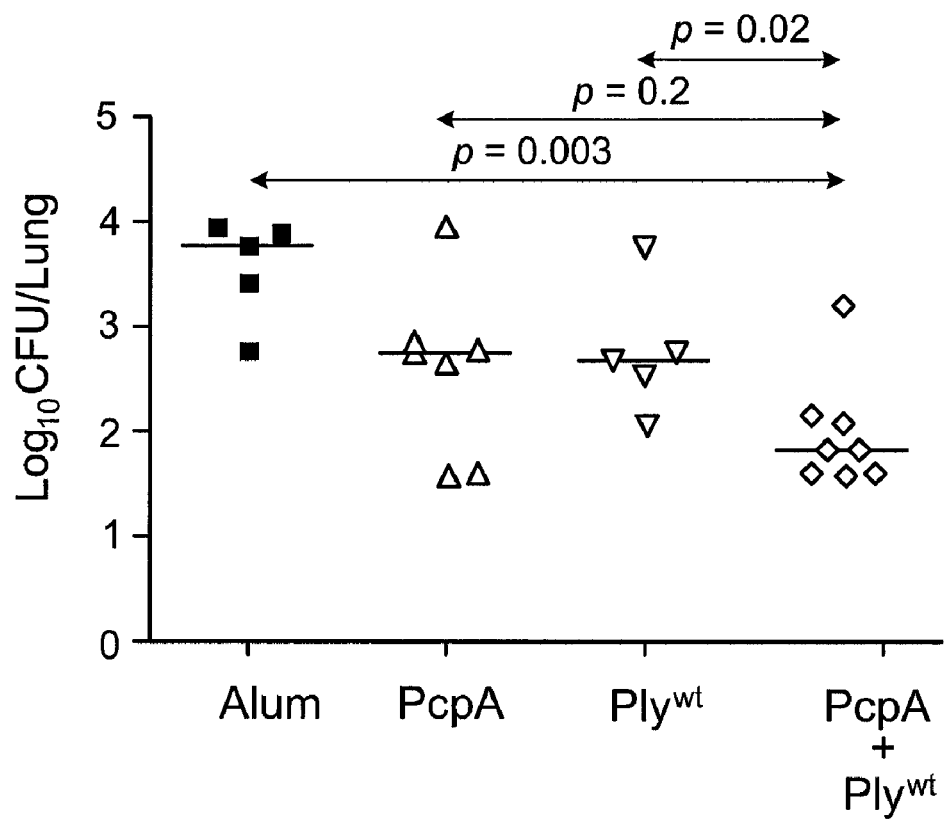
FIG. 13 shows protection against lung infection with PcpA and pneumolysin (Ply). Mice were immunized three times with 5 µg of rPcpA, 5 µg of pneumolysin (Ply), or 5 µg of rPcpA plus 5 µg Ply. The first two injections were with alum and the third injection was with protein alone. The Ply used was wild-type Ply. Mice were anethesized with isoflurane (MinRAD, Buffalo, N.Y.) and challenged i.n. with $5\times10^6$ CFU of capsular type 19F strain EF3030 in 40 µL volume. This procedure results in lung infection and nasal colonization. Seven days later mice were sacrificed and homogenized lungs were plated. The CFU observed indicated that immunization with either PcpA or Ply resulted in similar levels of protection. Mice immunized with PcpA and Ply resulted in over 100-fold more protection than control mice and 10 times more protection than Ply or PcpA alone.

Pneumolysin (Ply) is another protein that can elicit some protection against lung infection (Miles et al., *J. Infect. Dis.* 188:339-48 (2003)). Since pneumolysin and PcpA are both candidates for use in protein-based pneumococcal vaccines, it was determined whether the two proteins produce better protection against lung infection when both are used as immunogens than when either one is used alone. Mice were immunized three times with 5 µg of PcpA, 5 µg pneumolysin, or 5 µg of PcpA plus 5 µg of pneumolysin. The first two injections were with alum and the third injections were with protein alone. The pneumolysin used here was wild-type pneumolysin. FIG. 13 shows that pneumolysin elicits similar protection against lung infection to that elicited by PcpA. The combination of PcpA and pneumolysin was significantly more protective than pneumolysin alone. These data indicate that protection can be conferred using both PcpA and pneumolysin.

Example 7

Cross-Protection Against Other Pneumococci

To determine whether PcpA elicits cross protection, strains in addition to those described in Examples 1-2 can be tested using the methods described above. For studies of sepsis, strains such as WU2, A66, BG7322, EF6796, D39 in addition to TIGR4 are tested. These strains are of capsular types 3, 3, 6B, 6A, and 2. To examine lung infection, strains that work well in a mouse model of focal lung infection are used. These strains include EF9309, TG0893, L82016, BG7322 and EF6796. These are capsular types 23F, 14, 6B, 6B, and 6A.

Example 8

Presence of PcpA in Mice

CD1 outbred mice or CBA mice are infected with pneumococci in colonization, pneumonia and fatal sepsis models. Biological samples from lung wash, nasal wash, blood, and urine are obtained. Samples from mice with colonization and pneumonia are collected 6 days after inoculation. Samples from mice with sepsis following IN inoculation will be collected at 2 or 3 days post infection. EF3030 (type 19F), TJ0893, type 14, and EF9393 (type 23) are used for focal pneumonia. These strains cause focal pneumonia when $5 \times 10^5$ CFU are administered IN in 40 µl of Ringer's injection solution while mice are anesthetized. If the same number of CFU is given IN in 10 µl of Ringers without anesthesia mice are colonized but never achieve more than a couple hundred CFU in their lungs. To achieve pneumonia followed by sepsis mice will be given strains L82016 (type 6B) and TIGR4 (type 4). All of these strains can also be used in colonization models.

Mouse urine is collected by picking the mice up and holding the animal over a collection tube. The mice are also anesthetized with isoflurane (Attane; Minrad Inc), and bled by heart puncture, and serum was collected. The mice are then euthanized with an overdose of $CO_2$ and tested with a tail pinch to make sure they are unconscious. Next the trachea is severed and 0.5 ml of Ringers solution are pushed though the trachea and out the nose to obtain a nasal wash. The lungs are likewise lavaged with 0.5 ml of Ringers to obtain a lung wash. The washed nasal tissue and lung tissue from each mouse is homogenized in 0.5 ml volumes.

Each sample obtained from each mouse is quantitated by plating on blood agar plates to confirm disease in the mouse and to determine the numbers of live pneumococci, if any, in the particular fluid sample or tissue extract.

Each sample is assayed for PcpA content in serial dilution using ELISA capture assay. The PcpA is detected on whole pneumococci, pneumococcal fragments, or as a free protein released during autolysis of pneumococci in vivo. PcpA is observed in the lung wash or lung homogenate of mice with focal or septic lung infections but not from colonized mice even though the numbers of CFU seen in colonization with these strains is similar in colonization as well as focal pneumonia. Little to no PcpA is observed in a nasal wash of mice that are colonized or mice with lung infection.

Example 9

Presence of PcpA in Humans

Biological samples from a subject are assayed in a capture ELISA. AP-conjugated antibody used to detect the antibody in the top level of the sandwich is pre-absorbed so that it does not cross-react with the antibody used to capture the PcpA on the microtiter plate surface. One way to do this is to use the same species of antibody to detect the second layer of anti-PcpA as was used for the first layer. For example, if the plate is coated with rabbit anti-PcpA as a capture reagent and a mouse anti-PcpA is used to detect the bound PcpA, then if a commercial rabbit anti-mouse reagent is used to detect the mouse antibody to PcpA, there should be no reactivity of this antibody with the rabbit Ig used to initially coat the plates. Another approach can be to use a AP-conjugated IgG-specific MAb to develop the assay.

A positive control for this assay is a recombinant rPcpA of known concentration. After the concentration of the rPcpA is determined, it is diluted in 1% BSA, aliquoted and stored frozen at −80° C. A second positive control is a lysate of pneumococci grown in low Mn2+ conditions so that it contains PcpA. This lysate is aliquoted and stored at −80° C. Since the standard contains a known concentration of PcpA, based on protein assay, the exact sensitivity of the assay is known and nanogram concentrations of PcpA is determined in each fluid examined. Negative controls in the assay include a) the use of normal rabbit serum instead of the capture serum, b) the use of normal mouse serum in place of the detection serum, c) the absence of any PcpA containing solution (samples from non-infected mice or humans), and d) the absence of the anti-mouse Ig AP-conjugated rabbit antibodies. PcpA is detected on whole pneumococci, pneumococcal fragments, or as a free protein released during autolysis of pneumococci in vivo. PcpA observed in the biological samples indicates the subject has pneumonia. Little to no PcpA is observed in a nasal wash of subjects that are colonized.

Example 10

Use of Ratio of a Colonization Antigen and an Invasive Antigens to Diagnose Pneumonia Pneumonia can be diagnosed by determining the ratio of the concentration of an invasive antigen such as, for example, PcpA to the concentration of a colonization antigen such as, for example, NanA. The detection of NanA is done with a capture ELISA using antibodies to NanA. High ratios of PcpA:NanA are associated with pneumonia while low ratios of PcpA:NanA are associated with the absence of pneumonia. For example, a ratio of 2:1, PcpA:NanA, indicates pneumococcal pneumonia in the subject while a ratio of 1:2, PcpA:NanA, indicates the subject does not have pneumococcal pneumonia. This approach may help eliminate any false positives due to antigens produced during minimal invasion that is sometimes associated with colonization (Briles et al. Infect. Immun. 73:6945-6951 (2005)).

Publications cited herein and the material for which they are cited are hereby specifically incorporated by reference in their entireties.

---

What is claimed is:

1. A method of diagnosing pneumococcal pneumonia in a subject comprising:
   a) obtaining a biological sample from a subject; and
   b) detecting in the biological sample the presence of one or more pneumococcal antigens selectively expressed during invasive disease in the presence of low concentrations of Mn2+, wherein at least one of the pneumococcal antigens is PcpA, and wherein the presence of the antigen indicates pneumococcal pneumonia in the subject.

2. The method of claim 1, wherein the biological sample is a biological fluid.

3. The method of claim 2, wherein the biological fluid is selected from the group consisting of blood, serum, sputum, lung lavage and urine.

4. The method of claim 1, wherein the biological sample is not from the nasal cavity of the subject.

5. The method of claim 1, wherein the subject is not bacteremic.

6. The method of claim 1, further comprising the step of detecting in the biological sample the presence of C-polysaccharide.

7. The method of claim 1, wherein the antigen is not expressed during colonization.

8. The method of claim 1, wherein the detecting step is carried out using an immunological method.

9. The method of claim 1, wherein the detecting step is carried out using ELISA.

10. The method of claim 1, wherein the method further comprises detecting one or more pneumococcal antigens selected from the group consisting of PsaA, PsaB, PsaC, rrgA, rrgB, rrgC and srtB.

* * * * *

SEQUENCE LISTING

```
<160> NUMBER OF SEQ ID NOS: 47

<210> SEQ ID NO 1
<211> LENGTH: 192
<212> TYPE: PRT
<213> ORGANISM: Streptococcus pneumoniae

<400> SEQUENCE: 1

Leu Glu Lys Ile Glu Asp Arg Ala Phe Asp Phe Ser Glu Leu Glu Glu
 1               5                  10                  15

Ile Glu Leu Pro Ala Ser Leu Glu Tyr Ile Gly Thr Ser Ala Phe Ser
            20                  25                  30

Phe Ser Gln Lys Leu Lys Lys Leu Thr Phe Ser Ser Ser Ser Lys Leu
        35                  40                  45

Glu Leu Ile Ser His Glu Ala Phe Ala Asn Leu Ser Asn Leu Glu Lys
    50                  55                  60

Leu Thr Leu Pro Lys Ser Val Lys Thr Leu Gly Ser Asn Leu Phe Arg
65                  70                  75                  80

Leu Thr Thr Ser Leu Asn Met Leu Met Leu Arg Gly Met Ile Val Ala
                85                  90                  95

Ser Val Asp Gly Val Ser Phe Gln Ser Lys Thr Gln Leu Ile Tyr Tyr
            100                 105                 110

Pro Ser Gln Lys Asn Asp Glu Ser Tyr Lys Thr Pro Lys Glu Thr Lys
        115                 120                 125

Glu Leu Ala Ser Tyr Ser Phe Asn Lys Asn Ser Tyr Leu Lys Lys Leu
    130                 135                 140

Glu Leu Asn Glu Gly Leu Gln Lys Ile Gly Thr Phe Ala Phe Ala Asp
145                 150                 155                 160

Ala Thr Lys Leu Glu Glu Ile Ser Leu Pro Asn Ser Leu Glu Thr Ile
                165                 170                 175

Glu Arg Leu Ala Phe Tyr Gly Asn Leu Glu Leu Lys Glu Leu Ile Leu
            180                 185                 190

<210> SEQ ID NO 2
<211> LENGTH: 195
<212> TYPE: PRT
<213> ORGANISM: Streptococcus pneumoniae
```

<400> SEQUENCE: 2

```
Leu Glu Lys Ile Glu Asp Arg Ala Phe Asp Phe Ser Glu Leu Glu Glu
  1               5                  10                  15

Ile Glu Leu Pro Ala Ser Leu Glu Tyr Ile Gly Thr Ser Ala Phe Ser
             20                  25                  30

Phe Ser Gln Lys Leu Lys Lys Leu Thr Phe Ser Ser Ser Lys Leu
         35                  40                  45

Glu Leu Ile Ser His Glu Ala Phe Ala Asn Leu Ser Asn Leu Glu Lys
 50                  55                  60

Leu Thr Leu Pro Lys Ser Val Lys Thr Leu Gly Ser Asn Leu Phe Arg
 65                  70                  75                  80

Leu Thr Thr Ser Leu Lys His Val Asp Val Glu Glu Gly Asn Glu Ser
             85                  90                  95

Phe Ala Ser Val Asp Gly Val Leu Phe Ser Lys Asp Lys Thr Gln Leu
             100                 105                 110

Ile Tyr Tyr Pro Ser Gln Lys Asn Asp Glu Ser Tyr Lys Thr Pro Lys
             115                 120                 125

Glu Thr Lys Glu Leu Ala Ser Tyr Ser Phe Asn Lys Asn Ser Tyr Leu
 130                 135                 140

Lys Lys Leu Glu Leu Asn Glu Gly Leu Glu Lys Ile Gly Thr Phe Ala
145                 150                 155                 160

Phe Ala Asp Ala Ile Lys Leu Glu Glu Ile Ser Leu Pro Asn Ser Leu
             165                 170                 175

Glu Thr Ile Glu Arg Leu Ala Phe Tyr Gly Asn Leu Gly Leu Lys Glu
             180                 185                 190

Leu Ile Leu
        195
```

<210> SEQ ID NO 3
<211> LENGTH: 379
<212> TYPE: PRT
<213> ORGANISM: Streptococcus pneumoniae

<400> SEQUENCE: 3

```
Tyr Val Pro Asn Glu Pro Ile Leu Ala Ala Tyr Val Pro Asn Glu Pro
  1               5                  10                  15

Ile Leu Ala Asp Thr Pro Ser Ser Glu Val Ile Lys Glu Thr Lys Val
             20                  25                  30

Gly Ser Ile Ile Gln Gln Asn Asn Ile Lys Tyr Lys Val Leu Thr Val
         35                  40                  45

Glu Gly Asn Ile Gly Thr Val Gln Val Gly Asn Gly Val Thr Pro Val
 50                  55                  60

Glu Phe Glu Ala Gly Gln Asp Gly Lys Pro Phe Thr Ile Pro Thr Lys
 65                  70                  75                  80

Ile Thr Val Gly Asp Lys Val Phe Thr Val Thr Glu Val Ala Ser Gln
             85                  90                  95

Ala Phe Ser Tyr Tyr Pro Asp Glu Thr Gly Arg Ile Val Tyr Tyr Pro
             100                 105                 110

Ser Ser Ile Thr Ile Pro Ser Ser Ile Lys Lys Ile Gln Lys Lys Gly
             115                 120                 125

Phe His Gly Ser Lys Ala Lys Thr Ile Ile Phe Asp Lys Gly Ser Gln
 130                 135                 140

Leu Glu Lys Ile Glu Asp Arg Ala Phe Asp Phe Ser Glu Leu Glu Glu
145                 150                 155                 160
```

```
Ile Glu Leu Pro Ala Ser Leu Glu Tyr Ile Gly Thr Ser Ala Phe Ser
                165                 170                 175

Phe Ser Gln Lys Leu Lys Lys Leu Thr Phe Ser Ser Ser Lys Leu
        180                 185                 190

Glu Leu Ile Ser His Glu Ala Phe Ala Asn Leu Ser Asn Leu Glu Lys
        195                 200                 205

Leu Thr Leu Pro Lys Ser Val Lys Thr Leu Gly Ser Asn Leu Phe Arg
        210                 215                 220

Leu Thr Thr Ser Leu Asn Met Leu Met Leu Arg Gly Met Ile Val Ala
225                 230                 235                 240

Ser Val Asp Gly Val Ser Phe Gln Ser Lys Thr Gln Leu Ile Tyr Tyr
                245                 250                 255

Pro Ser Gln Lys Asn Asp Glu Ser Tyr Lys Thr Pro Lys Glu Thr Lys
                260                 265                 270

Glu Leu Ala Ser Tyr Ser Phe Asn Lys Asn Ser Tyr Leu Lys Lys Leu
                275                 280                 285

Glu Leu Asn Glu Gly Leu Gln Lys Ile Gly Thr Phe Ala Phe Ala Asp
        290                 295                 300

Ala Thr Lys Leu Glu Glu Ile Ser Leu Pro Asn Ser Leu Glu Thr Ile
305                 310                 315                 320

Glu Arg Leu Ala Phe Tyr Gly Asn Leu Glu Leu Lys Glu Leu Ile Leu
                325                 330                 335

Pro Asp Asn Val Lys Asn Phe Gly Lys His Val Met Asn Gly Leu Pro
                340                 345                 350

Lys Phe Leu Thr Leu Ser Gly Asn Asn Ile Asn Ser Leu Pro Ser Phe
        355                 360                 365

Phe Leu Ser Gly Val Leu Asp Ser Leu Lys Glu
        370                 375

<210> SEQ ID NO 4
<211> LENGTH: 373
<212> TYPE: PRT
<213> ORGANISM: Streptococcus pneumoniae

<400> SEQUENCE: 4

Tyr Val Pro Asn Glu Pro Ile Leu Ala Asp Thr Pro Ser Ser Glu Val
1               5                   10                  15

Ile Lys Glu Thr Lys Val Gly Ser Ile Gln Gln Asn Asn Ile Lys
            20                  25                  30

Tyr Lys Val Leu Thr Val Glu Gly Asn Ile Gly Thr Val Gln Val Gly
            35                  40                  45

Asn Gly Val Thr Pro Val Glu Phe Glu Ala Gly Gln Asp Gly Lys Pro
        50                  55                  60

Phe Thr Ile Pro Thr Lys Ile Thr Val Gly Asp Lys Val Phe Thr Val
65                  70                  75                  80

Thr Glu Val Ala Ser Gln Ala Phe Ser Tyr Tyr Pro Asp Glu Thr Gly
                85                  90                  95

Arg Ile Val Tyr Tyr Pro Ser Ser Ile Thr Ile Pro Ser Ser Ile Lys
                100                 105                 110

Lys Ile Gln Lys Lys Gly Phe His Gly Ser Lys Ala Lys Thr Ile Ile
            115                 120                 125

Phe Asp Lys Gly Ser Gln Leu Glu Lys Ile Glu Asp Arg Ala Phe Asp
        130                 135                 140

Phe Ser Glu Leu Glu Glu Ile Glu Leu Pro Ala Ser Leu Glu Tyr Ile
145                 150                 155                 160
```

```
Gly Thr Ser Ala Phe Ser Phe Ser Gln Lys Leu Lys Lys Leu Thr Phe
                165                 170                 175

Ser Ser Ser Ser Lys Leu Glu Leu Ile Ser His Glu Ala Phe Ala Asn
            180                 185                 190

Leu Ser Asn Leu Glu Lys Leu Thr Leu Pro Lys Ser Val Lys Thr Leu
        195                 200                 205

Gly Ser Asn Leu Phe Arg Leu Thr Thr Ser Leu Lys His Val Asp Val
    210                 215                 220

Glu Glu Gly Asn Glu Ser Phe Ala Ser Val Asp Gly Val Leu Phe Ser
225                 230                 235                 240

Lys Asp Lys Thr Gln Leu Ile Tyr Tyr Pro Ser Gln Lys Asn Asp Glu
                245                 250                 255

Ser Tyr Lys Thr Pro Lys Glu Thr Lys Glu Leu Ala Ser Tyr Ser Phe
            260                 265                 270

Asn Lys Asn Ser Tyr Leu Lys Lys Leu Glu Leu Asn Glu Gly Leu Glu
        275                 280                 285

Lys Ile Gly Thr Phe Ala Phe Ala Asp Ala Ile Lys Leu Glu Glu Ile
    290                 295                 300

Ser Leu Pro Asn Ser Leu Glu Thr Ile Glu Arg Leu Ala Phe Tyr Gly
305                 310                 315                 320

Asn Leu Glu Leu Lys Glu Leu Ile Leu Pro Asn Asn Val Lys Asn Phe
                325                 330                 335

Gly Lys His Val Met Asn Gly Leu Pro Lys Leu Lys Ser Leu Thr Ile
            340                 345                 350

Gly Asn Asn Ile Asn Ser Leu Pro Ser Phe Phe Leu Ser Gly Val Leu
        355                 360                 365

Asp Ser Leu Lys Glu
    370

<210> SEQ ID NO 5
<211> LENGTH: 10
<212> TYPE: PRT
<213> ORGANISM: Streptococcus pneumoniae

<400> SEQUENCE: 5

Leu Glu Lys Ile Glu Asp Arg Ala Phe Asp
1               5                   10

<210> SEQ ID NO 6
<211> LENGTH: 10
<212> TYPE: PRT
<213> ORGANISM: Streptococcus pneumoniae

<400> SEQUENCE: 6

Phe Ser Glu Leu Glu Glu Ile Glu Leu Pro
1               5                   10

<210> SEQ ID NO 7
<211> LENGTH: 10
<212> TYPE: PRT
<213> ORGANISM: Streptococcus pneumoniae

<400> SEQUENCE: 7

Ala Ser Leu Glu Tyr Ile Gly Thr Ser Ala
1               5                   10

<210> SEQ ID NO 8
<211> LENGTH: 10
<212> TYPE: PRT
<213> ORGANISM: Streptococcus pneumoniae
```

```
<400> SEQUENCE: 8

Phe Ser Phe Ser Gln Lys Leu Lys Lys Leu
 1               5                  10

<210> SEQ ID NO 9
<211> LENGTH: 10
<212> TYPE: PRT
<213> ORGANISM: Streptococcus pneumoniae

<400> SEQUENCE: 9

Thr Phe Ser Ser Ser Ser Lys Leu Glu Leu
 1               5                  10

<210> SEQ ID NO 10
<211> LENGTH: 10
<212> TYPE: PRT
<213> ORGANISM: Streptococcus pneumoniae

<400> SEQUENCE: 10

Ile Ser His Glu Ala Phe Ala Asn Leu Ser
 1               5                  10

<210> SEQ ID NO 11
<211> LENGTH: 10
<212> TYPE: PRT
<213> ORGANISM: Streptococcus pneumoniae

<400> SEQUENCE: 11

Asn Leu Glu Lys Leu Thr Leu Pro Lys Ser
 1               5                  10

<210> SEQ ID NO 12
<211> LENGTH: 10
<212> TYPE: PRT
<213> ORGANISM: Streptococcus pneumoniae

<400> SEQUENCE: 12

Val Lys Thr Leu Gly Ser Asn Leu Phe Arg
 1               5                  10

<210> SEQ ID NO 13
<211> LENGTH: 10
<212> TYPE: PRT
<213> ORGANISM: Streptococcus pneumoniae

<400> SEQUENCE: 13

Leu Thr Thr Ser Leu Asn Met Leu Met Leu
 1               5                  10

<210> SEQ ID NO 14
<211> LENGTH: 10
<212> TYPE: PRT
<213> ORGANISM: Streptococcus pneumoniae

<400> SEQUENCE: 14

Leu Thr Thr Ser Leu Lys His Val Asp Val
 1               5                  10

<210> SEQ ID NO 15
<211> LENGTH: 10
<212> TYPE: PRT
<213> ORGANISM: Streptococcus pneumoniae
```

```
<400> SEQUENCE: 15

Arg Gly Met Ile Val Ala Ser Val Asp Gly
 1               5                  10

<210> SEQ ID NO 16
<211> LENGTH: 12
<212> TYPE: PRT
<213> ORGANISM: Streptococcus pneumoniae

<400> SEQUENCE: 16

Glu Glu Gly Asn Glu Ser Phe Ala Ser Val Asp Gly
 1               5                  10

<210> SEQ ID NO 17
<211> LENGTH: 10
<212> TYPE: PRT
<213> ORGANISM: Streptococcus pneumoniae

<400> SEQUENCE: 17

Val Ser Phe Gln Ser Lys Thr Gln Leu Ile
 1               5                  10

<210> SEQ ID NO 18
<211> LENGTH: 11
<212> TYPE: PRT
<213> ORGANISM: Streptococcus pneumoniae

<400> SEQUENCE: 18

Val Leu Phe Ser Lys Asp Lys Thr Gln Leu Ile
 1               5                  10

<210> SEQ ID NO 19
<211> LENGTH: 10
<212> TYPE: PRT
<213> ORGANISM: Streptococcus pneumoniae

<400> SEQUENCE: 19

Tyr Tyr Pro Ser Gln Lys Asn Asp Glu Ser
 1               5                  10

<210> SEQ ID NO 20
<211> LENGTH: 10
<212> TYPE: PRT
<213> ORGANISM: Streptococcus pneumoniae

<400> SEQUENCE: 20

Tyr Lys Thr Pro Lys Glu Thr Lys Glu Leu
 1               5                  10

<210> SEQ ID NO 21
<211> LENGTH: 10
<212> TYPE: PRT
<213> ORGANISM: Streptococcus pneumoniae

<400> SEQUENCE: 21

Ala Ser Tyr Ser Phe Asn Lys Asn Ser Tyr
 1               5                  10

<210> SEQ ID NO 22
<211> LENGTH: 10
<212> TYPE: PRT
<213> ORGANISM: Streptococcus pneumoniae
```

```
<400> SEQUENCE: 22

Leu Lys Lys Leu Glu Leu Asn Glu Gly Leu
 1               5                  10

<210> SEQ ID NO 23
<211> LENGTH: 10
<212> TYPE: PRT
<213> ORGANISM: Streptococcus pneumoniae

<400> SEQUENCE: 23

Gln Lys Ile Gly Thr Phe Ala Phe Ala Asp
 1               5                  10

<210> SEQ ID NO 24
<211> LENGTH: 10
<212> TYPE: PRT
<213> ORGANISM: Streptococcus pneumoniae

<400> SEQUENCE: 24

Glu Lys Ile Gly Thr Phe Ala Phe Ala Asp
 1               5                  10

<210> SEQ ID NO 25
<211> LENGTH: 10
<212> TYPE: PRT
<213> ORGANISM: Streptococcus pneumoniae

<400> SEQUENCE: 25

Ala Thr Lys Leu Glu Glu Ile Ser Leu Pro
 1               5                  10

<210> SEQ ID NO 26
<211> LENGTH: 10
<212> TYPE: PRT
<213> ORGANISM: Streptococcus pneumoniae

<400> SEQUENCE: 26

Ala Ile Lys Leu Glu Glu Ile Ser Leu Pro
 1               5                  10

<210> SEQ ID NO 27
<211> LENGTH: 10
<212> TYPE: PRT
<213> ORGANISM: Streptococcus pneumoniae

<400> SEQUENCE: 27

Asn Ser Leu Glu Thr Ile Glu Arg Leu Ala
 1               5                  10

<210> SEQ ID NO 28
<211> LENGTH: 12
<212> TYPE: PRT
<213> ORGANISM: Streptococcus pneumoniae

<400> SEQUENCE: 28

Phe Tyr Gly Asn Leu Glu Leu Lys Glu Leu Ile Leu
 1               5                  10

<210> SEQ ID NO 29
<211> LENGTH: 122
<212> TYPE: PRT
<213> ORGANISM: Streptococcus pneumoniae
```

<400> SEQUENCE: 29

Ser Ser Glu Val Ile Lys Glu Thr Lys Val Gly Ser Ile Ile Gln Gln
1               5                   10                  15

Asn Asn Ile Lys Tyr Lys Val Leu Thr Val Glu Gly Asn Ile Gly Thr
            20                  25                  30

Val Gln Val Gly Asn Gly Val Thr Pro Val Glu Phe Glu Ala Gly Gln
        35                  40                  45

Asp Gly Lys Pro Phe Thr Ile Pro Thr Lys Ile Thr Val Gly Asp Lys
    50                  55                  60

Val Phe Thr Val Thr Glu Val Ala Ser Gln Ala Phe Ser Tyr Tyr Pro
65                  70                  75                  80

Asp Glu Thr Gly Arg Ile Val Tyr Tyr Pro Ser Ser Ile Thr Ile Pro
                85                  90                  95

Ser Ser Ile Lys Lys Ile Gln Lys Lys Gly Phe His Gly Ser Lys Ala
            100                 105                 110

Lys Thr Ile Ile Phe Asp Lys Gly Ser Gln
            115                 120

<210> SEQ ID NO 30
<211> LENGTH: 43
<212> TYPE: PRT
<213> ORGANISM: Streptococcus pneumoniae

<400> SEQUENCE: 30

Pro Asp Asn Val Lys Asn Phe Gly Lys His Val Met Asn Gly Leu Pro
1               5                   10                  15

Lys Phe Leu Thr Leu Ser Gly Asn Asn Ile Asn Ser Leu Pro Ser Phe
            20                  25                  30

Phe Leu Ser Gly Val Leu Asp Ser Leu Lys Glu
            35                  40

<210> SEQ ID NO 31
<211> LENGTH: 44
<212> TYPE: PRT
<213> ORGANISM: Streptococcus pneumoniae

<400> SEQUENCE: 31

Pro Asp Asn Val Lys Asn Phe Gly Lys His Val Met Asn Gly Leu Pro
1               5                   10                  15

Lys Leu Lys Ser Leu Thr Ile Gly Asn Asn Ile Asn Ser Leu Pro Ser
            20                  25                  30

Phe Phe Leu Ser Gly Val Leu Asp Ser Leu Lys Glu
            35                  40

<210> SEQ ID NO 32
<211> LENGTH: 2127
<212> TYPE: DNA
<213> ORGANISM: Streptococcus pneumoniae

<400> SEQUENCE: 32
atgaaaaaaa ctacaatatt atcattaact acagctgcgg ttattttagc agcatatgtc      60
cctaatgaac caatcctagc agcatatgtc cctaatgaac caatcctagc agatactcct    120
agttcggaag taatcaaaga gactaaagtt ggaagtatta ttcaacaaaa taatatcaaa    180
tataaggttc taactgtaga aggtaacata ggaactgttc aagtgggtaa tggagttact    240
cctgtagagt ttgaagctgg tcaagatgga aaaccattca cgattcctac aaaaatcaca    300
gtaggtgata agtatttac cgttactgaa gtagctagtc aagcttttag ttattatcca    360

-continued

```
gatgaaacag gtagaattgt ctactatcct agctctatta ctatcccatc aagcataaaa      420
aaaatacaaa aaaaaggctt ccatggaagt aaagctaaaa ctattatttt tgacaaaggc      480
agtcagctgg agaaaattga agatagagct tttgatttt ctgaattaga agagattgaa       540
ttgcctgcat ctctagaata tattggaaca agtgcatttt cttttagtca aaaattgaaa     600
aagctaacct tttcctcaag ttcaaaatta gaattaatat cacatgaggc ttttgctaat     660
ttatcaaatt tagagaaact aacattacca aaatcggtta aaacattagg aagtaatcta     720
tttagactca ctactagctt aaacatgttg atgttgagag aatgatcgt tgcctcagtt     780 gatggtgttt cgtttcaaag taaaactcaa ttaatттtatt atccaagtca aaaaatgac     840 gaaagttata aaacgcctaa ggagacaaaa gaacttgcat catattcgtt aataaaaat     900 tcttacttga aaaactcga attgaatgaa ggtttacaaa aaatcggtac ttttgcattt     960
gcggatgcga ccaaacttga agaaattagc ttaccaaata gtttagaaac tattgaacgt    1020
ttagcctttt acggtaattt agaattaaaa gaacttatat taccagataa tgttaaaaat    1080
tttggtaaac acgttatgaa cggtttacca aaatttttaa cattatctgg taataatatc    1140
aactcattgc cgtccttctt cctaagtggc gtcttagatt cattaaagga aattcatatt    1200
aagaataaaa gtacagagtt ttctgtgaaa aaagatacat ttgcaattcc tgaaactgtt    1260
aagttctatg taacatcaga acatataaaa gatgttctta aatcaaattt atctactagt    1320
aatgatatca ttgttgaaaa agtagataat ataaaacaag aaactgatgt agctaaacct    1380
aaaaagaatt ctaatcaggg agtagttggt tgggttaaag acaaaggttt atggtattac    1440

ttaaacgaat caggttcaat ggctactggt tgggttaaag acaaaggttt atggtattac    1500

ttaaacgaat caggttcaat ggctactggt tgggttaaag acaaaggttt atggtattac    1560

ttaaatgaat caggttcaat ggctactggt tgggttaaag acaaaggctt atggtattac    1620

ttaaacgaat caggttcaat ggctactggt tgggttaaag acaaaggctt atggtattac    1680

ttaaacgaat caggttcaat ggctactggt tgggttaaag acaaaggctt atggtattac    1740

ttaaatgaat caggttcaat ggctactggt tgggttaaag acaaaggctt atggtattac    1800

ttaaacgaat caggttcaat ggctactggt tgggttaaag acaaaggctt atggtattac    1860

ttaaatgaat caggttcaat ggctactggt tgggttaaag acaaaggctt atggtattac    1920

ttaaacgaat caggttcaat ggctactggt tgggttaaag acaaaggctt atggtattac    1980

ttaaacgaat caggttcaat ggctactggt tgggttaaag acaaaggctt atggtattac    2040

ttaaatgaat caggttcaat ggctactggt tggtttaaag tttctggtaa atggtactat    2100
acctataatt caggagattt tattttag                                          2127
```

<210> SEQ ID NO 33
<211> LENGTH: 2106
<212> TYPE: DNA
<213> ORGANISM: Streptococcus pneumoniae

<400> SEQUENCE: 33

```
atgaaaaaaa ctacaatatt atcattaact acagctgcgg ttatttagc agatgtccct       60 aatgaaccaa tcctagcaga tactcccagt tcggaagtaa tcaaagagac taaagttgga     120
agtattattc aacaaaataa tatcaaatat aaggttctaa ctgtagaagg taacatagga     180
actgttcaag tggtaatgg agttactcct gtagagtttg aagctggtca agatggaaaa     240
ccattcacga ttcctacaaa aatcacagta ggtgataaag tatttaccgt tactgaagta    300
gctagtcaag cttttagtta ttatccagat gaaacaggta gaattgtcta ctatcctagc    360
```

```
tctattacta tcccatcaag cataaaaaaa atacaaaaaa aaggcttcca tggaagtaaa      420
gctaaaacta ttatttttga caaaggcagt cagctggaga aaattgaaga tagagctttt      480 gattttctg aattagaaga gattgaattg cctgcatctc tagaatatat tggaacaagt       540 gcatttctt ttagtcaaaa attgaaaaag ctaacctttt cctcaagttc aaaattagaa       600
ttaatatcac atgaggcttt tgctaattta tcaaatttag agaaactaac attaccaaaa     660
tcggttaaaa cattaggaag taatctattt agactcacta ctagcttaaa acatgttgat     720
gttgaagaag gaaatgaatc gtttgcctca gttgatggtg ttttgttttc aaaagataaa     780
acccaattaa tttattatcc aagtcaaaaa aatgacgaaa gttataaaac gcctaaggag     840
acaaaagaac ttgcatcata ttcgtttaat aaaaattctt acttgaaaaa actcgaattg     900
aatgaaggtt tagaaaaaat cggtacttt gcatttgcag atgcgattaa acttgaagaa      960
attagcttac caaatagttt agaaactatt gaacgtttag ccttttacgg taatttagaa    1020
ttaaaagaac ttatattacc aaataatgtt aaaaattttg gtaaacacgt tatgaacggt    1080
ttaccaaaat taaaaagttt aacaattggt aataatatca actcattgcc gtccttcttc    1140
ctaagtggcg tcttagattc attaaaggaa attcatatta agaataaaag tacagagttt    1200
tctgtgaaaa aagatacatt tgcaattcct gaaactgtta agttctatgt aacatcagaa    1260
catataaaag atgttcttaa atcaaattta tctactagta atgatatcat tgttgaaaaa    1320
gtagataata taaaacaaga aactgatgta gctaaaccta aaaagaattc taatcaggga    1380
gtagttggtt gggttaaaga caaaggttta tggtattact taaacgaatc aggttcaatg    1440
gctactggtt gggttaaaga caaaggttta tggtattact taaacgaatc aggttcaatg    1500
gctactggtt gggttaaaga caaaggttta tggtattact taaatgaatc aggttcaatg    1560
gctactggtt gggttaaaga caaaggctta tggtattact taaacgaatc aggttcaatg    1620
gctactggtt gggttaaaga caaaggctta tggtattact taaacgaatc aggttcaatg    1680
gctactggtt gggttaaaga caaaggctta tggtattact taaatgaatc aggttcaatg    1740
gctactggtt gggttaaaga caaaggctta tggtattact taaacgaatc aggttcaatg    1800
gctactggtt gggttaaaga caaaggctta tggtattact taaatgaatc aggttcaatg    1860
gctactggtt gggttaaaga caaaggctta tggtattact taaacgaatc aggttcaatg    1920
gctactggtt gggttaaaga caaaggctta tggtattact taaacgaatc aggttcaatg    1980
gctactggtt gggttaaaga caaaggctta tggtattact taaatgaatc aggttcaatg    2040
gctactggtt ggtttaaagt ttctggtaaa tggtactata cctataattc aggagatttt    2100
atttag                                                                 2106

<210> SEQ ID NO 34
<211> LENGTH: 393
<212> TYPE: DNA
<213> ORGANISM: Streptococcus pneumoniae

<400> SEQUENCE: 34
ttagagaaac taacattacc aaaatcggtt aaaacattag gaagtaatct atttagactc       60
actactagct taaacatgtt gatgttgaga ggaatgatcg ttgcctcagt tgatggtgtt      120
tcgtttcaaa gtaaaactca attaatttat tatccaagtc aaaaaaatga cgaaagttat     180
aaaacgccta aggagacaaa agaacttgca tcatattcgt ttaataaaaa ttcttacttg     240
aaaaaactcg aattgaatga aggtttacaa aaaatcggta cttttgcatt tgcggatgcg     300
```

```
accaaacttg aagaaattag cttaccaaat agtttagaaa ctattgaacg tttagccttt      360
tacggtaatt tagaattaaa agaacttata tta                                   393

<210> SEQ ID NO 35
<211> LENGTH: 544
<212> TYPE: DNA
<213> ORGANISM: Streptococcus pneumoniae

<400> SEQUENCE: 35
ttagagaaac taacattacc aaaatcggtt aaaacattag gaagtaatct atttagactc       60
actactagct taaaacatgt tgatgttgaa gaaggaaatg aatcgtttgc ctcagttgat      120
ggtgttttgt tttcaaaaga taaaacccaa ttaatttatt atccaagtca aaaaaatgac      180
gaaagttata aaacgcctaa ggagacaaaa gaacttgcat catattcgtt taataaaaat      240
tcttacttga aaaaactcga attgaatgaa ggtttagaaa aaatcggtac ttttgcattt      300
gcagatgcga ttaaacttga agaaattagc ttaccaaata gtttagaaac tattgaacgt      360
ttagcctttt acggtaattt agaattaaaa gaacttatat taccaaataa tgttaaaaat      420
tttggtaaac acgttatgaa cggtttacca aaattaaaaa gtttaacaat tggtaataat      480
atcaactcat tgccgtcctt cttcctaagt ggcgtcttag attcattaaa ggaaattcat      540
atta                                                                   544

<210> SEQ ID NO 36
<211> LENGTH: 1137
<212> TYPE: DNA
<213> ORGANISM: Streptococcus pneumoniae

<400> SEQUENCE: 36
tatgtcccta atgaaccaat cctagcagca tatgtcccta atgaaccaat cctagcagat       60
actcctagtt cggaagtaat caaagagact aaagttggaa gtattattca acaaaataat      120
atcaaatata aggttctaac tgtagaaggt aacataggaa ctgttcaagt gggtaatgga      180
gttactcctg tagagtttga agctggtcaa gatggaaaac cattcacgat tcctacaaaa      240
atcacagtag gtgataaagt atttaccgtt actgaagtag ctagtcaagc ttttagttat      300
tatccagatg aaacaggtag aattgtctac tatcctagct ctattactat cccatcaagc      360
ataaaaaaaa tacaaaaaaa aggcttccat ggaagtaaag ctaaaactat tatttttgac      420
aaaggcagtc agctggagaa aattgaagat agagcttttg attttctga attagaagag       480 attgaattgc ctgcatctct agaatatatt ggaacaagtg catttctttt tagtcaaaaa      540
ttgaaaaagc taacctttc ctcaagttca aaattagaat aatatcaca tgaggctttt      600 gctaatttat caaatttaga gaaactaaca ttaccaaaat cggttaaaac attaggaagt      660 aatctatttta gactcactac tagcttaaac atgttgatgt tgagaggaat gatcgttgcc      720
tcagttgatg gtgtttcgtt tcaaagtaaa actcaattaa tttattatcc aagtcaaaaa      780
aatgacgaaa gttataaaac gcctaaggag acaaagaac ttgcatcata ttcgtttaat      840
aaaaattctt acttgaaaaa actcgaattg aatgaaggt tacaaaaaat cggtactttt      900
gcatttgcgg atgcgaccaa acttgaagaa attagcttac caaatagttt agaaactatt      960
gaacgtttag ccttttacgg taatttagaa ttaaagaac ttatattacc agataatgtt     1020
aaaaattttg gtaaacacgt tatgaacggt ttaccaaaat tttaacatt atctggtaat     1080 aatatcaact cattgccgtc cttcttccta agtggcgtct tagattcatt aaaggaa       1137
```

```
<210> SEQ ID NO 37
<211> LENGTH: 1119
<212> TYPE: DNA
<213> ORGANISM: Streptococcus pneumoniae

<400> SEQUENCE: 37
gatgtcccta atgaaccaat cctagcagat actcccagtt cggaagtaat caaagagact      60
aaagttggaa gtattattca acaaaataat atcaaatata aggttctaac tgtagaaggt     120
aacataggaa ctgttcaagt gggtaatgga gttactcctg tagagtttga agctggtcaa     180
gatggaaaac cattcacgat tcctacaaaa atcacagtag gtgataaagt atttaccgtt     240
actgaagtag ctagtcaagc ttttagttat tatccagatg aaacaggtag aattgtctac     300
tatcctagct ctattactat cccatcaagc ataaaaaaaa tacaaaaaaa aggcttccat     360
ggaagtaaag ctaaaactat tattttgac aaaggcagtc agctggagaa aattgaagat     420
agagcttttg attttctga attagaagag attgaattgc ctgcatctct agaatatatt     480
ggaacaagtg cattttcttt tagtcaaaaa ttgaaaaagc taccttttc ctcaagttca     540 aaattagaat aatatcaca tgaggctttt gctaatttat caaatttaga gaaactaaca     600
ttaccaaaat cggttaaaac attaggaagt aatctattta gactcactac tagcttaaaa     660
catgttgatg ttgaagaagg aaatgaatcg tttgcctcag ttgatggtgt tttgttttca     720
aaagataaaa cccaattaat ttattatcca gtcaaaaaa atgacgaaag ttataaaacg     780
cctaaggaga caaagaact tgcatcatat tcgtttaata aaaattctta cttgaaaaaa     840
ctcgaattga atgaaggttt agaaaaaatc ggtacttttg catttgcaga tgcgattaaa     900
cttgaagaaa ttagcttacc aaatagttta gaaactattg aacgtttagc cttttacggt     960
aatttagaat taaagaact tatattacca aataatgtta aaaattttgg taaacacgtt    1020
atgaacggtt taccaaaatt aaaaagttta acaattggta ataatatcaa ctcattgccg    1080
tccttcttcc taagtggcgt cttagattca ttaaaggaa                          1119

<210> SEQ ID NO 38
<211> LENGTH: 366
<212> TYPE: DNA
<213> ORGANISM: Streptococcus pneumoniae

<400> SEQUENCE: 38
agttcggaag taatcaaaga gactaaagtt ggaagtatta ttcaacaaaa taatatcaaa      60
tataaggttc taactgtaga aggtaacata ggaactgttc aagtgggtaa tggagttact     120
cctgtagagt ttgaagctgg tcaagatgga aaaccattca cgattcctac aaaaatcaca     180
gtaggtgata aagtatttac cgttactgaa gtagctagtc aagcttttag ttattatcca     240
gatgaaacag gtagaattgt ctactatcct agctctatta ctatcccatc aagcataaaa     300
aaaatacaaa aaaaggcttc catggaagta aaagctaaaa ctattattttt tgacaaaggc     360 agtcag                                                              366

<210> SEQ ID NO 39
<211> LENGTH: 27
<212> TYPE: DNA
<213> ORGANISM: Artificial Sequence
<220> FEATURE:
<223> OTHER INFORMATION: Synthetically generated oligonucleotide

<400> SEQUENCE: 39
cgcggatcca tatgtcccta atgaacc                                        27
```

```
<210> SEQ ID NO 40
<211> LENGTH: 49
<212> TYPE: DNA
<213> ORGANISM: Artificial Sequence
<220> FEATURE:
<223> OTHER INFORMATION: Synthetically generated oligonucleotide

<400> SEQUENCE: 40
gcgctcgagt tcctttaatg aatctaagac gccacttagg aagaaggac                    49

<210> SEQ ID NO 41
<211> LENGTH: 390
<212> TYPE: PRT
<213> ORGANISM: Artificial Sequence
<220> FEATURE:
<223> OTHER INFORMATION: Synthetic construct

<400> SEQUENCE: 41

Met Asp Ile Gly Ile Asn Ser Asp Pro Tyr Val Pro Asn Glu Pro Ile
1               5                   10                  15

Leu Ala Asp Thr Pro Ser Ser Glu Val Ile Lys Glu Thr Lys Val Gly
                20                  25                  30

Ser Ile Ile Gln Gln Asn Asn Ile Lys Tyr Lys Val Leu Thr Val Glu
            35                  40                  45

Gly Asn Ile Gly Thr Val Gln Val Gly Asn Gly Val Thr Pro Val Glu
        50                  55                  60

Phe Glu Ala Gly Gln Asp Gly Lys Pro Phe Thr Ile Pro Thr Lys Ile
65                  70                  75                  80

Thr Val Gly Asp Lys Val Phe Thr Val Thr Glu Val Ala Ser Gln Ala
                85                  90                  95

Phe Ser Tyr Tyr Pro Asp Glu Thr Gly Arg Ile Val Tyr Tyr Pro Ser
            100                 105                 110

Ser Ile Thr Ile Pro Ser Ser Ile Lys Lys Ile Gln Lys Lys Gly Phe
        115                 120                 125

His Gly Ser Lys Ala Lys Thr Ile Ile Phe Asp Lys Gly Ser Gln Leu
    130                 135                 140

Glu Lys Ile Glu Asp Arg Ala Phe Asp Phe Ser Glu Leu Glu Glu Ile
145                 150                 155                 160

Glu Leu Pro Ala Ser Leu Glu Tyr Ile Gly Thr Ser Ala Phe Ser Phe
                165                 170                 175

Ser Gln Lys Leu Lys Lys Leu Thr Phe Ser Ser Ser Lys Leu Glu
            180                 185                 190

Leu Ile Ser His Glu Ala Phe Ala Asn Leu Ser Asn Leu Glu Lys Leu
        195                 200                 205

Thr Leu Pro Lys Ser Val Lys Thr Leu Gly Ser Asn Leu Phe Arg Leu
    210                 215                 220

Thr Thr Ser Leu Lys His Val Asp Val Glu Glu Gly Asn Glu Ser Phe
225                 230                 235                 240

Ala Ser Val Asp Gly Val Leu Phe Ser Lys Asp Lys Thr Gln Leu Ile
                245                 250                 255

Tyr Tyr Pro Ser Gln Lys Asn Asp Glu Ser Tyr Lys Thr Pro Lys Glu
            260                 265                 270

Thr Lys Glu Leu Ala Ser Tyr Ser Phe Asn Lys Asn Ser Tyr Leu Lys
        275                 280                 285

Lys Leu Glu Leu Asn Glu Gly Leu Lys Ile Gly Thr Phe Ala Phe
    290                 295                 300

Ala Asp Ala Ile Lys Leu Glu Glu Ile Ser Leu Pro Asn Ser Leu Glu
305                 310                 315                 320
```

```
Thr Ile Glu Arg Leu Ala Phe Tyr Gly Asn Leu Glu Leu Lys Glu Leu
            325                 330                 335

Ile Leu Pro Asn Asn Val Lys Asn Phe Gly Lys His Val Met Asn Gly
        340                 345                 350

Leu Pro Lys Leu Lys Ser Leu Thr Ile Gly Asn Asn Ile Asn Ser Leu
    355                 360                 365

Pro Ser Phe Phe Leu Ser Gly Val Leu Asp Ser Leu Lys Glu Leu Glu
370                 375                 380

His His His His His His
385                 390

<210> SEQ ID NO 42
<211> LENGTH: 1162
<212> TYPE: DNA
<213> ORGANISM: Streptococcus pneumoniae

<400> SEQUENCE: 42
ggatccatat gtccctaatg aaccaatcct agcagcatat gtccctaatg aaccaatcct      60
agcagatact cccagttcgg aagtaatcaa agagactaaa gttggaagta ttattcaaca     120
aaataatatc aaatataagg ttctaactgt agaaggtaac ataggaactg ttcaagtggg     180
taatggagtt actcctgtag agtttgaagc tggtcaagat ggaaaaccat tcacgattcc     240
tacaaaaatc acagtaggtg ataaagtatt taccgttact gaagtagcta gtcaagcttt     300
tagttattat ccagatgaaa caggtagaat tgtctactat cctagctcta ttactatccc     360
atcaagcata aaaaaaatac aaaaaaaagg cttccatgga agtaaagcta aaactattat     420
ttttgacaaa ggcagtcagc tggagaaaat tgaagataga gcttttgatt tttctgaatt     480
agaagagatt gaattgcctg catctctaga atatattgga acaagtgcat tttcttttag     540
tcaaaaattg aaaaagctaa ccttttcctc aagttcaaaa ttagaattaa tatcacatga     600
ggcttttgct aatttatcaa atttagagaa actaacatta ccaaaatcgg ttaaaacatt     660
aggaagtaat ctatttagac tcactactag cttaaaacat gttgatgttg aagaaggaaa     720
tgaatcgttt gcctcagttg atggtgtttt gttttcaaaa gataaaaccc aattaattta     780
ttatccaagt caaaaaaatg acgaaagtta taaaacgcct aaggagacaa agaacttgc     840 atcatattcg tttaataaaa attcttactt gaaaaaactc gaattgaatg aaggtttaga     900
aaaaatcggt acttttgcat tgcagatgc gattaaactt gaagaaatta gcttaccaaa     960
tagtttagaa actattgaac gtttagcctt ttacggtaat ttagaattaa agaacttat    1020 attaccaaat aatgttaaaa attttggtaa acacgttatg aacggtttac caaaattaaa    1080
aagtttaaca attggtaata atatcaactc attgccgtcc ttcttcctaa gtggcgtctt    1140
agattcatta aaggaactcg ag                                             1162

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
aactgttcaa gtgggtaatg g                                               21

<210> SEQ ID NO 44
<211> LENGTH: 22
<212> TYPE: DNA
<213> ORGANISM: Artificial Sequence
```

<220> FEATURE:
<223> OTHER INFORMATION: Primer

<400> SEQUENCE: 44
tgaacttgag gaaaaggtta gc                                            22

<210> SEQ ID NO 45
<211> LENGTH: 38
<212> TYPE: DNA
<213> ORGANISM: Artificial Sequence
<220> FEATURE:
<223> OTHER INFORMATION: Primer

<400> SEQUENCE: 45
atgaaaaaac tacaatatta tcattaacta cagctgcg                           38

<210> SEQ ID NO 46
<211> LENGTH: 33
<212> TYPE: DNA
<213> ORGANISM: Artificial Sequence
<220> FEATURE:
<223> OTHER INFORMATION: Primer

<400> SEQUENCE: 46
ccataaacct ttgtctttaa cccaaccaac tac                                33

<210> SEQ ID NO 47
<211> LENGTH: 311
<212> TYPE: PRT
<213> ORGANISM: Streptococcus pneumoniae

<400> SEQUENCE: 47

Ile His Ile Lys Asn Lys Ser Thr Glu Phe Ser Val Lys Lys Asp Thr
1               5                   10                  15

Phe Ala Ile Pro Glu Thr Val Lys Phe Tyr Val Thr Ser Glu His Ile
                20                  25                  30

Lys Asp Val Leu Lys Ser Asn Leu Ser Thr Ser Asn Asp Ile Ile Val
            35                  40                  45

Glu Lys Val Asp Asn Ile Lys Gln Glu Thr Asp Val Ala Lys Pro Lys
    50                  55                  60

Lys Asn Ser Asn Gln Gly Val Val Gly Trp Val Lys Asp Lys Gly Leu
65                  70                  75                  80

Trp Tyr Tyr Leu Asn Glu Ser Gly Ser Met Ala Thr Gly Trp Val Lys
                85                  90                  95

Asp Lys Gly Leu Trp Tyr Tyr Leu Asn Glu Ser Gly Ser Met Ala Thr
            100                 105                 110

Gly Trp Val Lys Asp Lys Gly Leu Trp Tyr Tyr Leu Asn Glu Ser Gly
        115                 120                 125

Ser Met Ala Thr Gly Trp Val Lys Asp Lys Gly Leu Trp Tyr Tyr Leu
    130                 135                 140

Asn Glu Ser Gly Ser Met Ala Thr Gly Trp Val Lys Asp Lys Gly Leu
145                 150                 155                 160

Trp Tyr Tyr Leu Asn Glu Ser Gly Ser Met Ala Thr Gly Trp Val Lys
                165                 170                 175

Asp Lys Gly Leu Trp Tyr Tyr Leu Asn Glu Ser Gly Ser Met Ala Thr
            180                 185                 190

Gly Trp Val Lys Asp Lys Gly Leu Trp Tyr Tyr Leu Asn Glu Ser Gly
        195                 200                 205

Ser Met Ala Thr Gly Trp Val Lys Asp Lys Gly Leu Trp Tyr Tyr Leu
    210                 215                 220

```
Asn Glu Ser Gly Ser Met Ala Thr Gly Trp Val Lys Asp Lys Gly Leu
225                 230                 235                 240

Trp Tyr Tyr Leu Asn Glu Ser Gly Ser Met Ala Thr Gly Trp Val Lys
            245                 250                 255

Asp Lys Gly Leu Trp Tyr Tyr Leu Asn Glu Ser Gly Ser Met Ala Thr
        260                 265                 270

Gly Trp Val Lys Asp Lys Gly Leu Trp Tyr Tyr Leu Asn Glu Ser Gly
    275                 280                 285

Ser Met Ala Thr Gly Trp Phe Lys Val Ser Gly Lys Trp Tyr Tyr Thr
    290                 295                 300

Tyr Asn Ser Gly Asp Phe Ile
305             310
```